(12) United States Patent
McAuliffe et al.

(10) Patent No.: US 6,745,770 B2
(45) Date of Patent: Jun. 8, 2004

(54) FLOW DIVERTER FOR CONTROLLING THE PRESSURE AND FLOW RATE IN A CPAP DEVICE

(75) Inventors: Patrick J. McAuliffe, Carlingford (AU); Denis L. Bullock, Milton (AU)

(73) Assignee: ResMed Limited, North Ryde (AU)

( * ) Notice: Subject to any disclaimer, the term of this patent is extended or adjusted under 35 U.S.C. 154(b) by 71 days.

(21) Appl. No.: 10/038,583

(22) Filed: Jan. 8, 2002

(65) Prior Publication Data

US 2003/0127096 A1 Jul. 10, 2003

(51) Int. Cl.[7] .................. A62B 9/02; A61M 16/00
(52) U.S. Cl. .................. 128/205.24; 128/204.18
(58) Field of Search .................. 128/200.24, 204.18, 128/204.22, 204.23, 204.24, 204.25, 204.26, 205.24, 204.21, 201.28; 137/162, 625, 625.14, 625.12, 487.5

(56) References Cited

U.S. PATENT DOCUMENTS

| | | | | |
|---|---|---|---|---|
| 3,586,021 A | * | 6/1971 | McGuinness | 128/204.24 |
| 4,061,155 A | | 12/1977 | Sopha | |
| 4,277,832 A | | 7/1981 | Wong | |
| 4,877,023 A | * | 10/1989 | Zalkin | 128/204.21 |
| 4,938,252 A | | 7/1990 | Piechnick | |
| 4,970,041 A | | 11/1990 | Reinhardt | |
| 4,976,237 A | | 12/1990 | Bollinger | |
| 5,040,569 A | | 8/1991 | Nogami et al. | |
| 5,349,983 A | | 9/1994 | Ozarowski et al. | |
| 5,474,062 A | | 12/1995 | DeVires et al. | |
| 5,507,282 A | * | 4/1996 | Younes | 128/204.21 |
| 5,522,416 A | | 6/1996 | Farrell et al. | |
| 5,598,838 A | | 2/1997 | Servidio et al. | |
| 5,678,541 A | * | 10/1997 | Garraffa | 128/205.24 |
| 5,878,765 A | | 3/1999 | Lange | |
| 5,931,160 A | * | 8/1999 | Gilmore et al. | 128/204.21 |
| 5,931,163 A | | 8/1999 | Stegmann et al. | |
| 6,209,540 B1 | * | 4/2001 | Sugiura et al. | 128/204.18 |
| 6,253,764 B1 | * | 7/2001 | Calluaud | 128/204.18 |
| 6,269,839 B1 | | 8/2001 | Wickham et al. | |
| 6,357,463 B1 | | 3/2002 | Wickham et al. | |
| 6,443,154 B1 | * | 9/2002 | Jalde et al. | 128/205.29 |
| 6,526,974 B1 | * | 3/2003 | Brydon et al. | 128/205.24 |

FOREIGN PATENT DOCUMENTS

| | | |
|---|---|---|
| EP | 0 086 259 A2 | 10/1982 |
| EP | 1 059 096 A2 | 12/2000 |
| WO | WO 97/10868 | 3/1997 |
| WO | WO 0/07651 | 2/2000 |

* cited by examiner

Primary Examiner—Aaron J. Lewis
Assistant Examiner—Teena Mitchell
(74) Attorney, Agent, or Firm—Nixon & Vanderhye P.C.

(57) ABSTRACT

A flow diverter valve is used in controlling the pressure and/or flow rate of a breathable gas supplied to the airways of a patient by a breathable gas flow generator supply apparatus during, for example, ventilatory assistance treatments such as non-invasive positive pressure ventilation and nasal Continuous Positive Airway Pressure (CPAP) treatment of Obstructive Sleep Apnea. The flow diverter valve includes a vane and a housing. The housing has an inlet port, an outlet port, and an exhaust port. The exhaust port opens to atmosphere, and the inlet port is in fluid communication with the flow generator. The outlet port is in fluid communication with a patient mask via a conduit. The vane is configured with respect to the housing such that a blower associated with the CPAP apparatus remains substantially unchoked, regardless of whether the vane is in the open or closed position.

20 Claims, 14 Drawing Sheets

FLOW DIVERTER FOR CONTROLLING THE PRESSURE AND FLOW RATE IN A CPAP DEVICE

RELATED ART

This application is related to pending U.S. patent application Ser. No. 09/598,053 filed on Jun. 21, 2001, describing a control member for a valve and method for determining fluid flow rate through a valve. This application is also related to U.S. patent application Ser. No. 09/642,824 filed on Aug. 22, 2000, describing pressure control in CPAP treatment or assisted respiration. International PCT Patent Application No. PCT/AU97/00631 describes varying pressure at a patient mask through the period of treatment during inspiration or expiration, and International PCT patent application No. PCT/AU96/00586 describes a flow diverting valve with a rotatable control member, both of which are related to this application. The contents of these U.S. and International PCT Patent Applications are incorporated herein by reference in their entireties. This application is also related to U.S. Pat. No. 4,944,310, which describes Continuous Positive Airway Pressure (CPAP) treatment, and U.S. Pat. No. 5,245,995 which describes automatically adjusting nasal CPAP treatment. The contents of these patents are incorporated herein by reference in their entireties.

BACKGROUND OF THE INVENTION

1. Field of the Invention

The present invention relates to a ventilatory assistance apparatus, and in particular, a ventilatory assistance apparatus including a flow diverter valve in fluid communication with a flow generator.

2. Background of the Invention

Non-Invasive Positive Pressure Ventilation (NIPPV) is a form of treatment for breathing disorders which can involve a relatively higher pressure of air or other breathable gas being provided to the entrance of a patient's airways via a patient mask during the inspiratory phase of respiration, and a relatively lower pressure or atmospheric pressure being provided in the patient mask during the expiratory phase of respiration. In other NIPPV modes the pressure can be made to vary in a complex manner throughout the respiratory cycle. For example, the pressure at the mask during inspiration or expiration can be varied through the period of treatment.

Continuous Positive Airway Pressure (CPAP) treatment is commonly used to treat breathing disorders including Obstructive Sleep Apnea (OSA). CPAP treatment continuously provides pressurized air or other breathable gas to the entrance of a patient's airways via a patient mask at a pressure elevated above atmospheric pressure, typically in the range 3–20 cm $H_2O$. CPAP treatment can act as a pneumatic splint of a patient's upper airway.

CPAP treatment can be in a number of forms, including the maintenance of a constant treatment pressure level, alternating between two different constant levels in synchronism with the inspiratory and expiratory phases of respiration ("bi-level CPAP"), and having an automatically adjustable and/or a computer controlled level in accordance with a patient's therapeutic needs. In all of these cases there is a need for control over the pressure of air or breathable gas supplied to the patient mask.

Breathable gas supply apparatus used in CPAP and NIPPV treatments broadly comprise a flow generator constituted by a continuous source of air or other breathable gas generally in the form of a blower driven by an electric motor. A pressurized supply of air or other breathable gas can also be used. The gas supply is connected to a conduit or tube, which is in turn connected to a patient mask (or nasal prong) which incorporates, or has in lose proximity, a vent to atmosphere for exhausting exhaled gases, such as carbon dioxide. To vary the flow supplied to the patient during inspiration and expiration, a valve member can be used, such as the valve member disclosed in U.S. patent application Ser. No. 09/598,053. For example, a cammed rotatable member can be used to permit a large flow during patient inspiration, and a relatively small (or substantively no) flow during patient expiration. However, this type of valve arrangement may be disadvantageous since during the patient expiration, when the valve member does not permit a significant, if any flow, the blower, which is upstream of the valve member, may be choked. Stated differently, flow through and from the blower may temporarily stop if the valve member is positioned to prevent or substantially prevent flow to the patient, e.g., when the patient is in the expiration phase of the breathing cycle. When inspiration resumes and the valve member rotates so as to permit flow or more flow to the patient, the fan or impeller associated with the blower may require a few revolutions (e.g., two) in order to reinstate flow through the impeller to the conduit and to the patient. As such, the response time of the CPAP apparatus when changing from the expiration to the inspiration may be delayed.

Treatment pressure of the air or other breathable gas can be controlled by speed control of the electric motor driving the blower of the flow generator. An example of a related art flow generator using a speed controlled blower is illustrated in FIG. 1. Conventional flow generator 110 is comprised by a chamber 112 that is segregated from a housing 114 of the flow generator 110. The housing 114 houses control circuitry (not shown) associated with the flow generator 110. The flow generator 110 is further comprised by a motor 116 driving an induced flow centrifugal turbine (impeller) 118, which induces the flow of air or breathable gas by an air inlet 120 to pass the air or breathable gas under pressure by an air outlet 122 to the air delivery tube (not shown) and so to the mask (also not shown). The turbine 118 has radially directed impeller blades 124. The alternate use of axial fans is known also in CPAP apparatus.

For typical CPAP treatment, the blower motor must be able to change its operational speed quickly. This results in the need to supply additional electrical power during times of operational speed increases. Disadvantages associated with rapid transitions in motor speed are, for example, noise, vibration, blower choking, and increased thermal dissipation requirements, in addition to increased power requirements.

Treatment pressure can alternatively be controlled by driving the electric motor of the blower at a constant speed, and venting or bleeding-off excess air from the output side of the blower. An example of this type of related art pressure control is shown in FIG. 2. A turbine 118 is connected to a plenum chamber 130 by a supply pipe 132. The plenum chamber 130 has a controllable spill valve 134 operable to indexingly open and close an opening 136 in the chamber wall to allow the venting of air to atmosphere so as to achieve the desired output pressure at an air outlet 138. Consequently, venting can be associated with excessive noise when the treatment pressure is adjusted. Additionally, it is difficult to maintain precise treatment pressure regulation and to maintain a high maximum flow rate, due in part to the large volume of plenum chamber 130. Imprecise treatment pressure regulation can lead to patient discomfort.

FIGS. 3A and 3B illustrate a prior art treatment pressure control using a bleeding valve 140 in fluid communication with blower 150 that is operated by a mechanism 142 situated within the flow path 144. In this embodiment, the mechanism 142 operates primarily in either an open position 146 (FIG. 3A) or a closed position 148 (FIG. 3B), resulting in imprecise, abrupt treatment pressure regulation. Additionally, the mechanism 142 situated in the flow path 144 can impede flow and cause noise, and can introduce into the flow path 144 odors and/or other contaminants generated during the operation of the mechanism 142. This results in patient discomfort and decreased patient compliance with treatment.

Noise and/or patient discomfort decrease patient compliance with treatment of breathing disorders. Therefore, there is a need in the prior art for an improved apparatus that increases patient compliance with treatment by reducing disadvantages including noise emissions and imprecise treatment pressure regulation. There is also a need to provide a valve arrangement that can prevent choking of the blower and/or improve the speed and/or response time when the ventilation changes from the expiration mode to the inspiration mode.

SUMMARY OF THE INVENTION

It is an aspect of the present invention to provide an improved flow diverter valve and, in a preferred form, a flow diverter valve with reduced noise and/or flow fluctuations and/or increased response speed.

It is another aspect to provide a valve assembly including a flow diverter vane that does not choke a blower with which it is associated, regardless of the position of the vane.

According to one preferred embodiment, there is provided a valve assembly for use in a ventilator, the valve assembly comprising a housing and a rotatable vane for directing the flow of air within the housing. The housing has an inlet port for receiving a flow of pressurized air from a blower, an outlet port for delivering air to a patient interface and an exhaust port. The vane is rotatable between a first angular position and a second angular position without choking the blower. In the first angular position, substantially all of the flow of air received at the inlet port is directed by the vane to the exhaust port. In the second angular position, substantially all of the flow of air received at the inlet port is directed by the vane to the outlet port. In angular positions intermediate of the first and second angular positions, a fraction of the flow of air received at the inlet port is directed by the vane to the exhaust port and the complementary fraction of the flow of air received at the inlet port is directed by the vane to the outlet port.

According to another embodiment, there is provided a ventilatory assistance apparatus comprising a flow generator and a flow diverter valve, in communication with the flow generator, including a housing defining an inlet port, an outlet port and an exhaust port. The exhaust port is positioned between the inlet port and the outlet port and is configured to exhaust at least one of flow from the inlet port and back flow from the outlet port. A vane moveable between an open position and a closed position can selectively protrude into the flow from the inlet port and thereby variably divert the flow from the inlet port to at least one of the exhaust port and the outlet port. The vane forms a portion of a passage leading to the outlet port when in the closed position.

In another embodiment, a flow diverter valve comprises a housing defining an inlet port and an outlet port, an exhaust port positioned between the inlet and outlet ports, and a vane moveable between an open position and a closed position. The vane can selectively protrude into the flow from the inlet port and thereby variably divert the flow from the inlet port to at least one of the exhaust port and the outlet port. The vane forms a portion of a passage leading to the outlet port when in the closed position.

In yet another embodiment, there is provided a CPAP apparatus comprising a flow generator and a flow diverter valve, in communication with the flow generator, including a housing defining an inlet port, an outlet port and an exhaust port. The exhaust port is positioned between the inlet port and the outlet port and is configured to exhaust at least one of flow from the inlet port and back flow from the outlet port. A vane moveable between an open position and a closed position can selectively admit undiverted flow from the inlet port to at least one of the exhaust port and the outlet port when the vane is in the open position.

In yet another embodiment, a flow diverter valve comprises a housing defining an inlet port and an outlet port, an exhaust port positioned between the inlet and outlet ports. A vane moveable between an open position and a closed position can selectively admit undiverted flow from the inlet port to at least one of the exhaust port and the outlet port when the vane is in the open position.

BRIEF DESCRIPTION OF THE DRAWINGS

These and other aspects of the invention will be described in or apparent from the following detailed description of preferred embodiments, wherein.

DETAILED DESCRIPTION OF PREFERRED EMBODIMENTS

Figure 1:
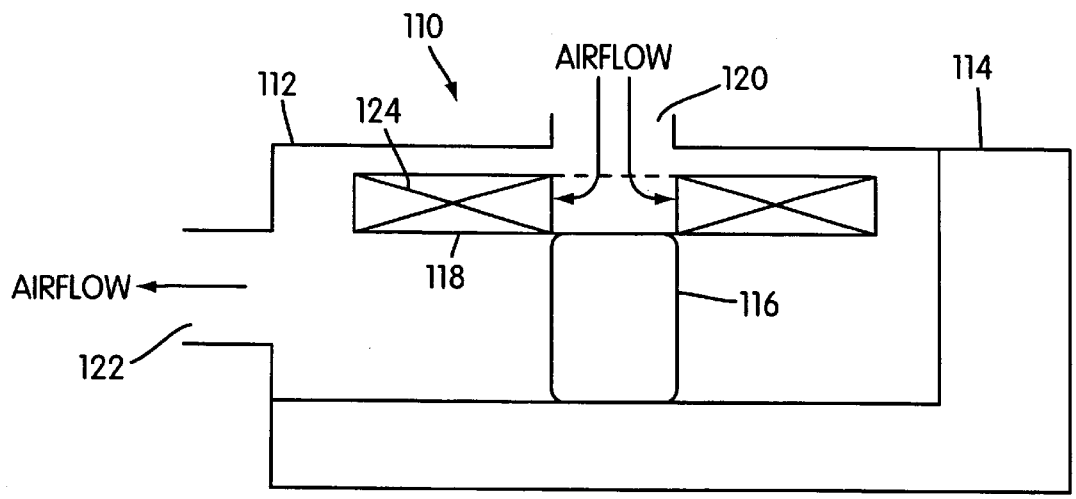
FIG. 1 is a side view of a controllable, variable flow generator in the related art.
Figure 2:
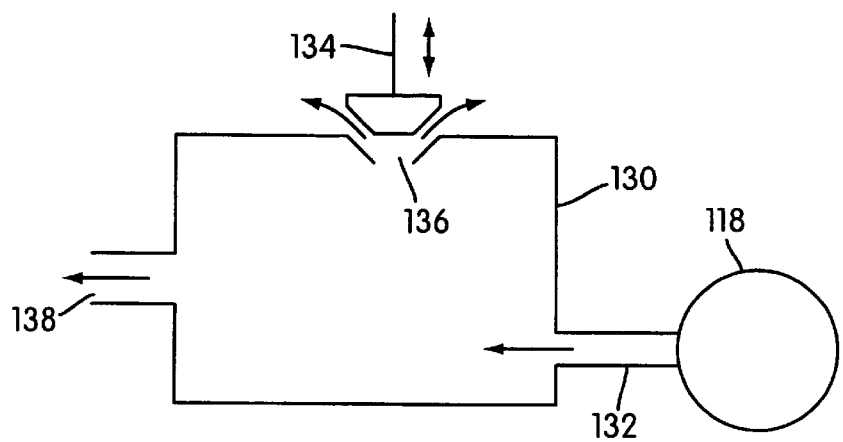
FIG. 2 is a side view of a controllable flow generator in the related art.
Figure 3A:
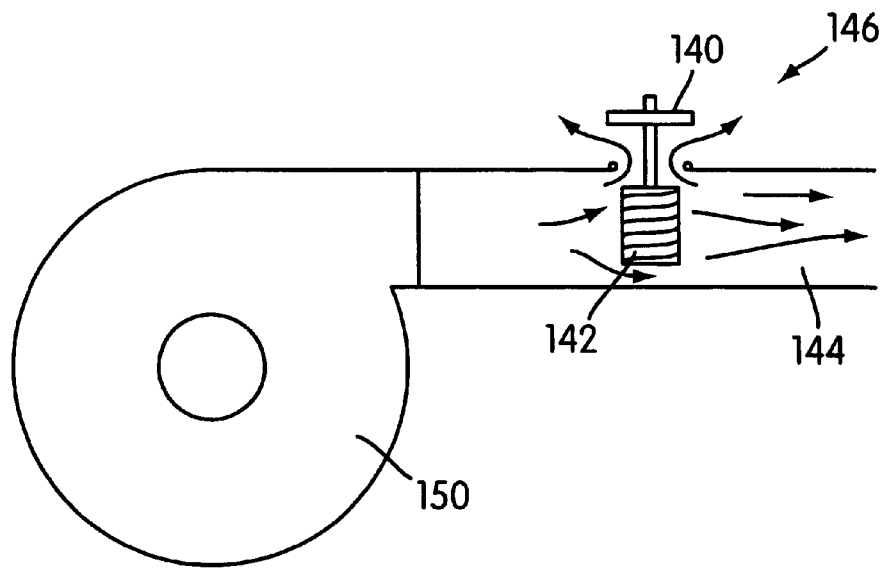
FIGS. 3A and 3B are side views of a controllable flow generator in the prior art.
Figure 3B:
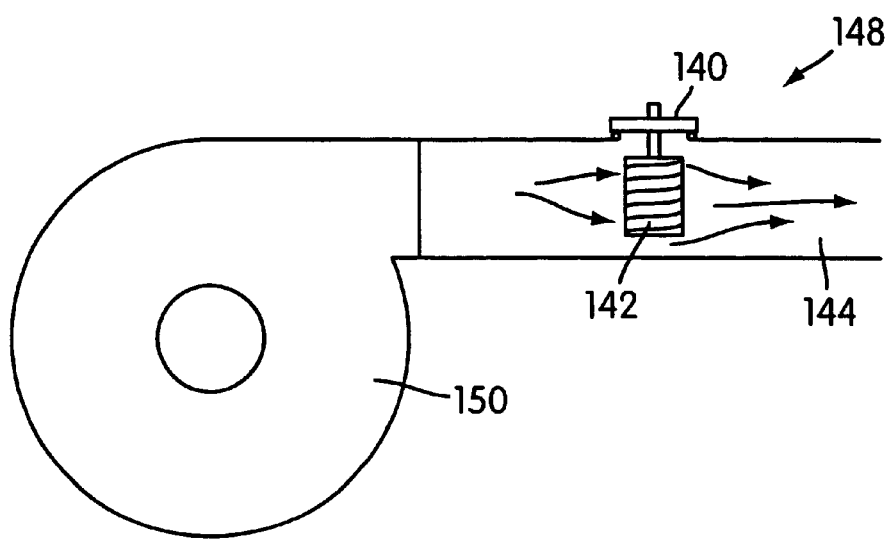
Figure 4:
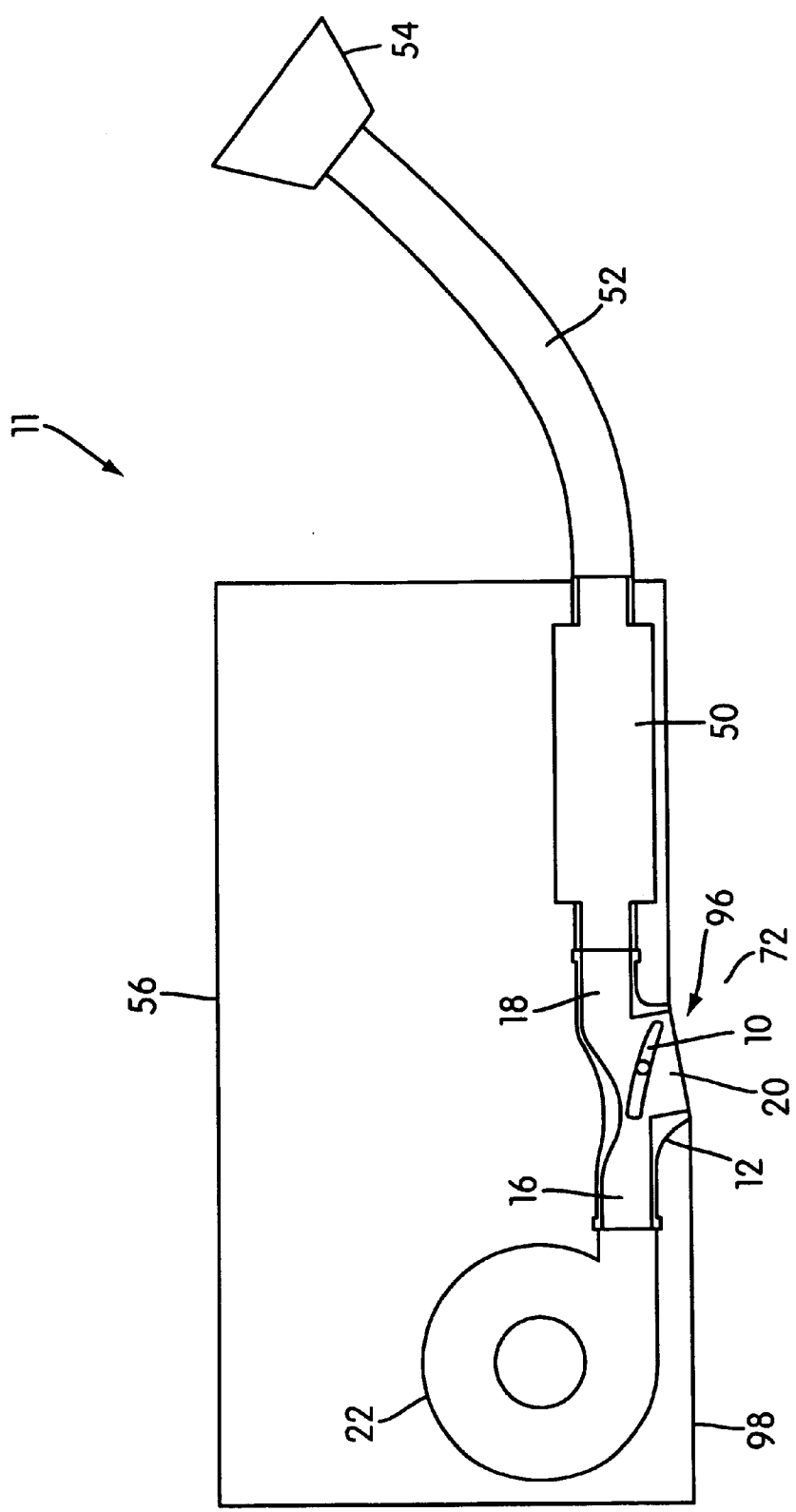
FIG. 4 is a top view of a ventilatory assistance apparatus according to an embodiment of the present invention.

A ventilatory assistance apparatus 11 according to an embodiment of the present invention is illustrated in FIG. 4. A flow generator 22, in fluid communication with a flow diverter valve 12 via an inlet port 16, provides a flow of air or breathable gas to the flow diverter valve 12 at a generally constant pressure, typically consistent with a maximum treatment pressure. Flow diverter valve 12 includes a vane 10 pivotably mounted within the flow diverter valve 12. Pressure and flow rate of the flow of air or breathable gas from the flow generator 22 are controlled by the flow diverter valve 12 and the vane 10. The flow diverter valve 12 is connected via an outlet port 18 in fluid communication with a flow meter 50, although alternate embodiments could incorporate the flow meter 50 integrally with the flow diverter valve 12. The flow meter 50 is connected in fluid communication with a patient mask 54 via a conduit 52. The flow generator 22, flow diverter valve 12, and flow meter 50 are enclosed within an apparatus body 56. The apparatus body 56 includes a side wall 98 with an apparatus body opening 96.

Figure 5:
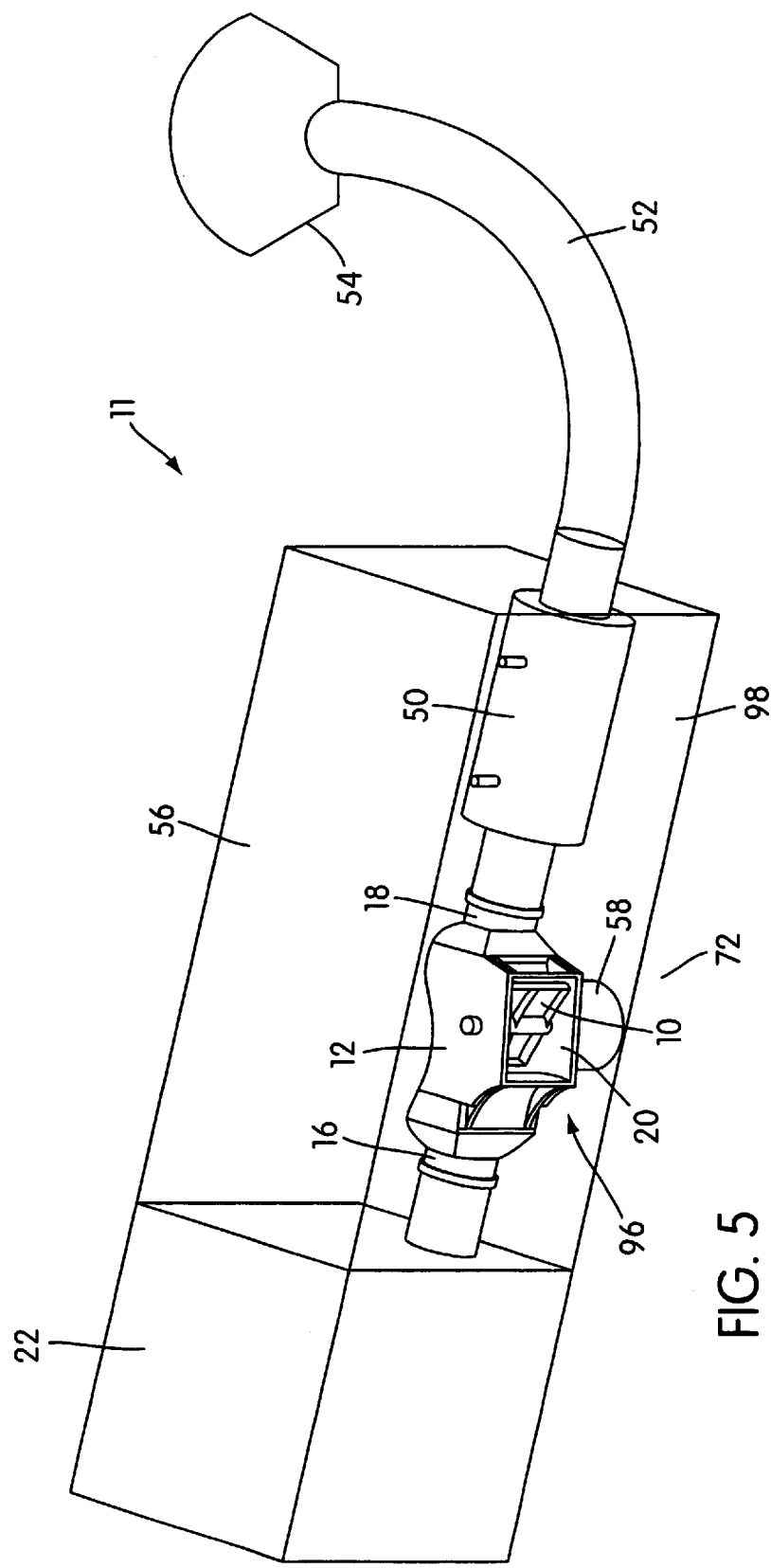
FIG. 5 is a perspective view of a ventilatory assistance apparatus according to an embodiment of the present invention.

FIG. 5 shows a perspective view of the ventilatory assistance apparatus 11 shown in FIG. 4. A rotary actuator 58 is shown mounted to the flow diverter valve 12. In the illustrated embodiment of FIGS. 4–5, the flow meter 50 is arranged within the apparatus body 56 downstream from the flow generator 22 and the flow diverter valve 12, so that turbulence and flow fluctuations within the flow meter 50 generated by the flow generator 22 are minimized. It is understood, however, that alternate arrangements or combinations of the flow generator 22, flow diverter valve 12, and flow meter 50 within the apparatus body 56 are possible.

The flow diverter valve 12 can be used in controlling the pressure and flow rate of a breathable gas supplied to the patient mask 54 during, for example, nasal Continuous Positive Airway Pressure (CPAP) treatment of Obstructive Sleep Apnea (OSA). However, it will be appreciated that the invention is not limited to these particular uses and is equally applicable to controlling the flow of any fluid (i.e., gas or liquid) passing a valve.

In this specification, any reference to the patient mask 54 is to be understood as incorporating a reference to a nasal mask, mouth mask, a nasal and mouth mask in combination, full face mask, nasal pillows or nasal prongs, unless otherwise specifically indicated. Any reference to CPAP treatment is to be understood as embracing all of the above-described forms of ventilatory treatment or assistance. All references to "treatment pressure" include a continuous pressure that can vary with time if desired in accordance with treatment needs, and therefore is not necessarily of a constant level.

Figure 6:
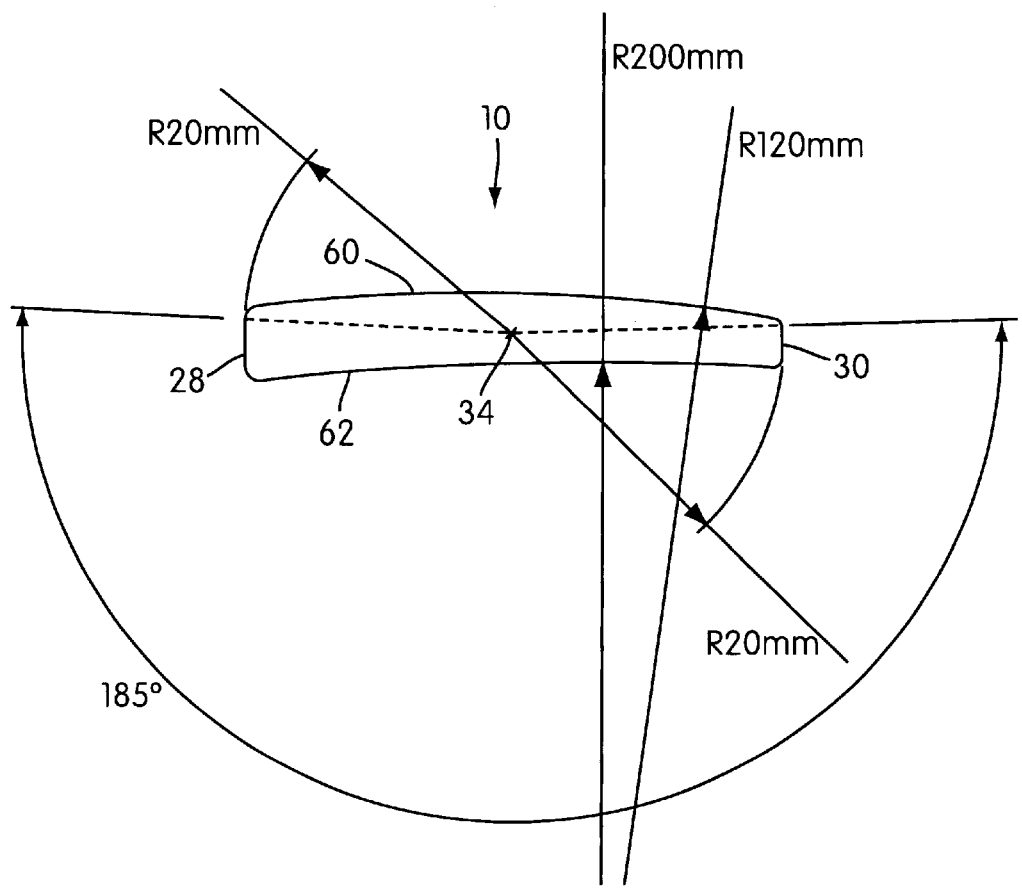
FIG. 6 is a top view showing the vane of FIGS. 4–5 in greater detail.

FIG. 6 shows the vane 10 of FIGS. 4 and 5 in more detail. A leading vane edge 28 and a trailing vane edge 30 of the vane 10 are curved concentric with a vane pivot axis 34. In the illustrated embodiment shown in FIG. 6, the vane pivot axis 34 is arranged centrally equidistant between the leading vane edge 28 and the trailing vane edge 30. This arrangement results in the leading vane edge 28 and the trailing vane edge 30 having equal radii of curvature about the vane pivot axis 34. Although illustrated as having equal radii of curvature of 20 mm, it is understood that a broad range of radii of curvature can be used, e.g., the radii can be different. The vane pivot axis 34 can be arranged non-equidistant from the leading vane edge 28 and the trailing vane edge 30, resulting in unequal radii of curvature of the leading vane edge 28 and the trailing vane edge 30 about the vane pivot axis 34.

Figure 7:
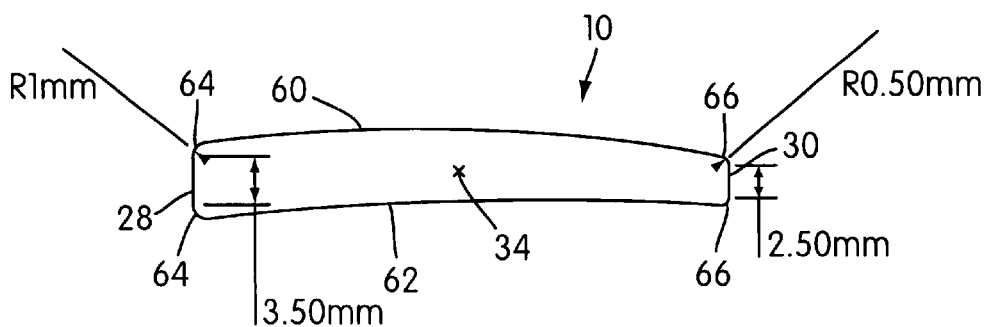
FIG. 7 is a top view showing additional details of the vane of FIG. 6.

In the illustrated embodiment, a first side vane surface 60 and a second side vane surface 62 of the vane 10 have radii of curvature greater than the radii of curvature of the leading vane edge 28 and the trailing vane edge 30. In particular, the first side vane surface 60 has a radius of curvature of 120 mm. The second side vane surface 62 has a radius of curvature of 200 mm. Alternatively, other radii can be used including a range of radii of curvature, preferably from between three to four times the radii of curvature of the leading vane edge 28 and the trailing vane edge 30, to radii of curvature of infinity (i.e., side vane surfaces 60 and 62 can be flat). The radii of curvature of the first side vane surface 60 and the second side vane surface 62 can be based on a portion of a National Advisory Committee for Aeronautics (NACA) airfoil section for improved flow characteristics. The convex curvature of the first side vane surface 60 and the second side vane surface 62 can curve upwards or downwards, or one surface can curve upwards and the other downwards, at least depending upon the desired aerodynamic characteristics. However, as shown in FIGS. 6 and 7, the surfaces 60, 62 preferably curve downward to minimize turbulence. As illustrated, the leading vane edge 28 and the trailing vane edge 30 extend along their respective radii of curvature until they intersect with the first side vane surface 60. As measured about the vane pivot axis 34 along the radii of curvature of the leading vane edge 28 and the trailing vane edge 30, the intersection points describe an arc of approximately 160°–210°, but is preferably 185°. Depending upon the particular aerodynamic characteristics desired for the vane 10, and the radii of curvature used for the first side vane surface 60 and the second side vane surface 62, arcs of varying degree can be used. A smaller radius of curvature used for the first side vane surface 60 results in a larger arc, and vice versa.

FIG. 7 shows additional details of the vane 10 of FIGS. 4–6. Leading vane corners 64, defined by the intersections of the leading vane edge 28 with the first side vane surface 60 and the second side vane surface 62, are rounded. Trailing vane corners 66, defined by the intersections of the trailing vane edge 30 with the first side vane surface 60 and the second side vane surface 62, are also rounded. The radii of curvature for the leading vane corners 64 and trailing vane corners 66 can vary depending on the particular embodiment. As shown in the embodiment of FIG. 7, the leading vane corners 64 have an approximate radius of curvature of 1 mm. The trailing vane corners 66 preferably have an approximate radius of curvature of 0.5 mm. Radii of curvature of the vane corners 64 and 66 can be determined by the manufacturing methods and actual width of the particular vane 10. Additionally, radii of curvature of the vane corners 64 and 66 can be chosen as large as possible while not greatly reducing the sealing area of the vane edges 28 and 30. Larger radii of curvature of the leading vane corners 64 are particularly beneficial to improved aerodynamic characteristics. The distance between the centers of the radii of curvature for the leading vane corners 64 can vary as well, although the distance is illustrated in this embodiment as 3.5 mm. Likewise the distance between the centers of the radii of curvature for the trailing vane corners 66 can vary and is illustrated as 2.5 mm. Preferably, a distance is chosen large enough to provide sufficient sealing area of the vane edges 28 and 30.

Figure 8:
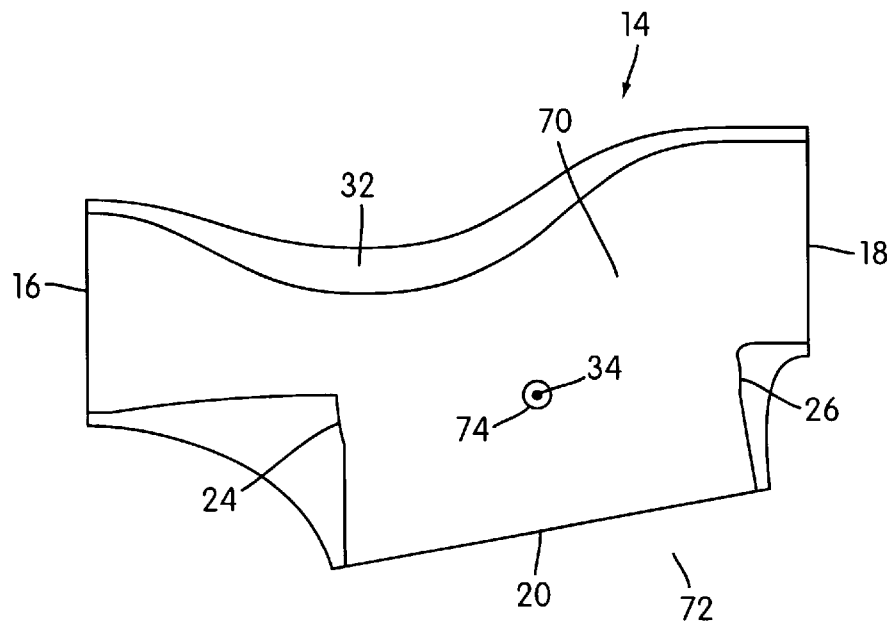
FIG. 8 is a top view showing the housing of FIGS. 4–5 in greater detail.
Figure 9:
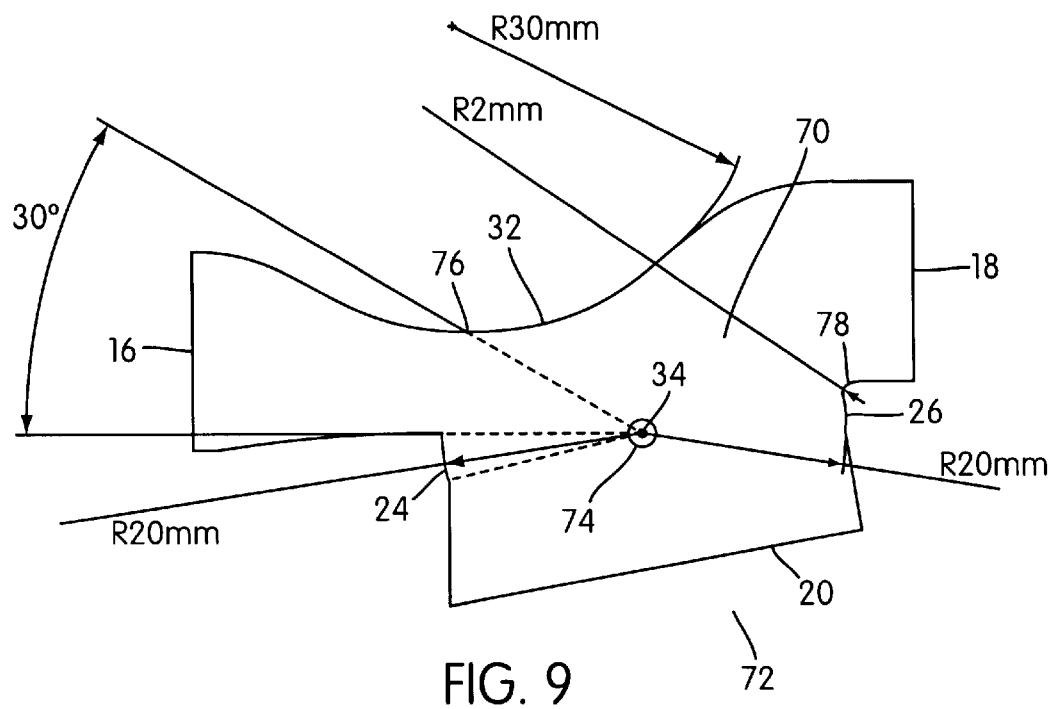
FIG. 9 is a top view showing the interior of the housing of FIG. 8 in greater detail.
Figure 10:
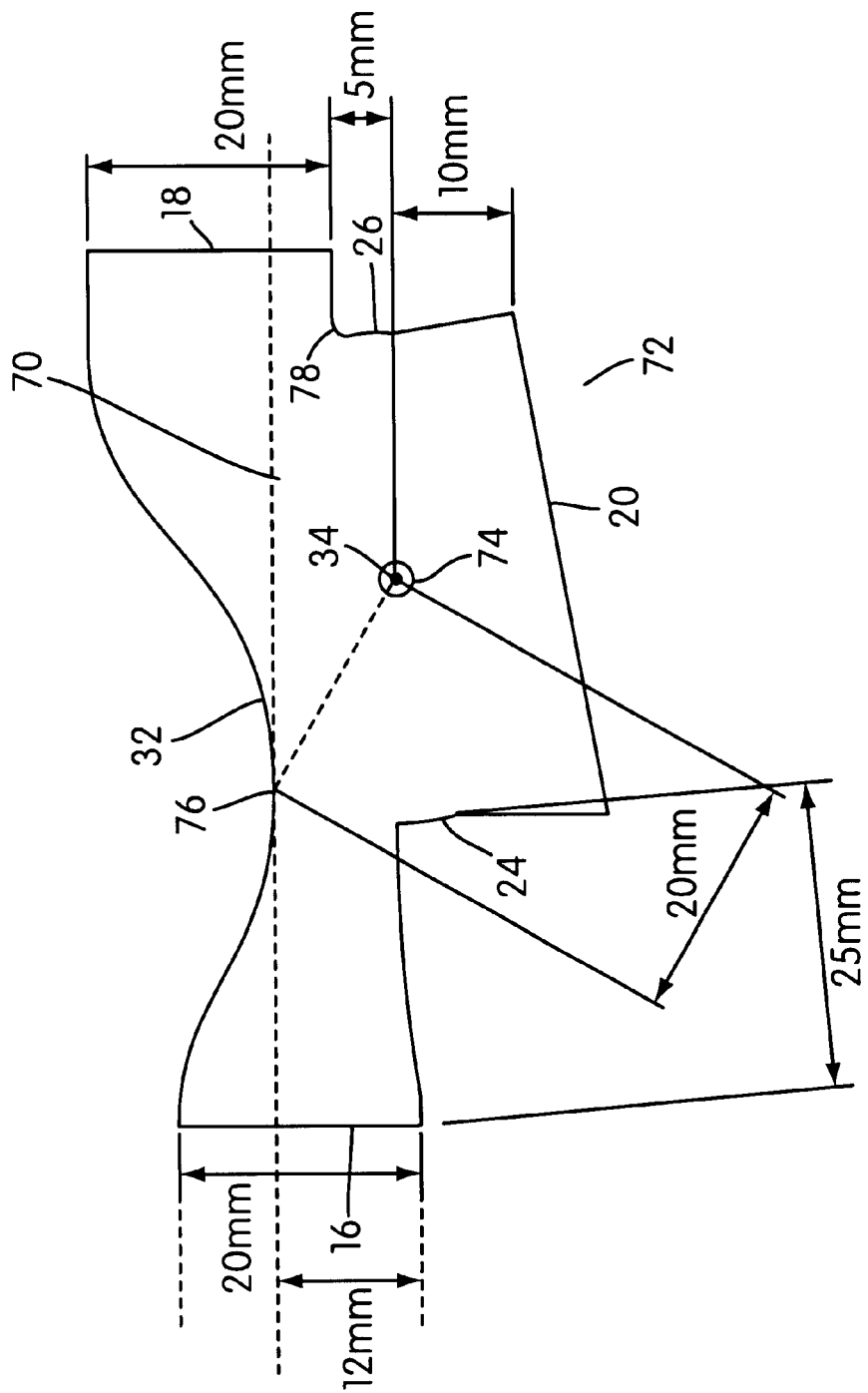
FIG. 10 is a top view showing additional details of the housing interior of FIG. 9.

The flow diverter valve 12 illustrated in FIGS. 4–5 includes a housing 14. The housing 14 is shown in more detail in FIGS. 8–10, illustrated without connecting portions 68 as shown in FIGS. 11–16. The inlet port 16 is in fluid communication with a housing interior 70, and the outlet port 18 is also in fluid communication with the housing interior 70. An exhaust port 20 in fluid communication with the housing interior 70 opens to atmosphere 72 via apparatus body opening 96. The housing 14 also includes a housing through hole 74 and a housing bend 32. The housing bend 32 is shaped to provide a smooth continuous curve from the inlet port 16 to the outlet port 18.

FIG. 9 illustrates in more detail the housing interior 70 of the housing 14 shown in FIG. 8. The housing bend 32 in this illustrated embodiment has a radius of curvature of 30 mm. A leading housing surface 24 and a trailing housing surface 26 have a radius of curvature of 20 mm, concentric with the housing through hole 74. Accordingly, the radii of curvature of the housing surfaces 24 and 26 vary with the width of the exhaust port 20. Likewise, the radii of curvature of the corresponding vane edges 28 and 30 which can seal against the housing surfaces 24 and 26 similarly vary with the width of the exhaust port. A housing bend intersection point 76 is defined by the intersection between the radius of curvature of the leading housing surface 24 and the housing bend 32. The distance between the housing bend 32 and the leading housing surface 24 has been chosen such that the angular distance, measured from the housing through hole 74, between the housing bend intersection point 76 and the leading housing surface 24 is approximately 30°. The angular distance can be varied depending upon factors including the speed and range of movement of the rotary actuator 58. In general, a smaller angular distance between the housing bend intersection point 76 and the leading housing surface 24 results in a faster response time for a given rotary actuator 58 with a given rotary response speed. However, a smaller angular distance between the housing bend intersection point 76 and the leading housing surface 24 results in a corresponding greater pressure drop across an imaginary line passing through the housing bend intersection point 76 and the leading housing surface 24, as compared to a larger angular distance. An outlet port bend 78 has a radius of curvature of 2 mm, variably chosen to provide a smooth flow path through the housing interior 70 without sharp changes of direction.

FIG. 10 shows various linear dimensions of the housing interior 70 shown in the embodiment of FIGS. 8–9. The inlet port 16 and the outlet port 18 have openings 20 mm wide, to accommodate other components (not shown) connected to the inlet port 16 and the outlet port 18, the particular opening sizes not intrinsic to the function of the flow diverter valve 12. The width of the inlet port 16 is narrowed by the housing bend 32 such that the width is reduced to 12 mm in the housing interior 70. The distance between the housing bend intersection point 76 and the housing through hole 74 is 20 mm, the distance from the trailing housing surface 26 along the exhaust port 20 to the atmosphere 72 is 10 mm, and the distance from the trailing housing surface 26 to the outlet port 18 is 20 mm. The distance from the outlet port 16 to the leading housing surface 24 is 25 mm. These distances are chosen to provide a smooth flow path throughout the housing interior 70 without presenting sharp changes of direction.

Figure 11:
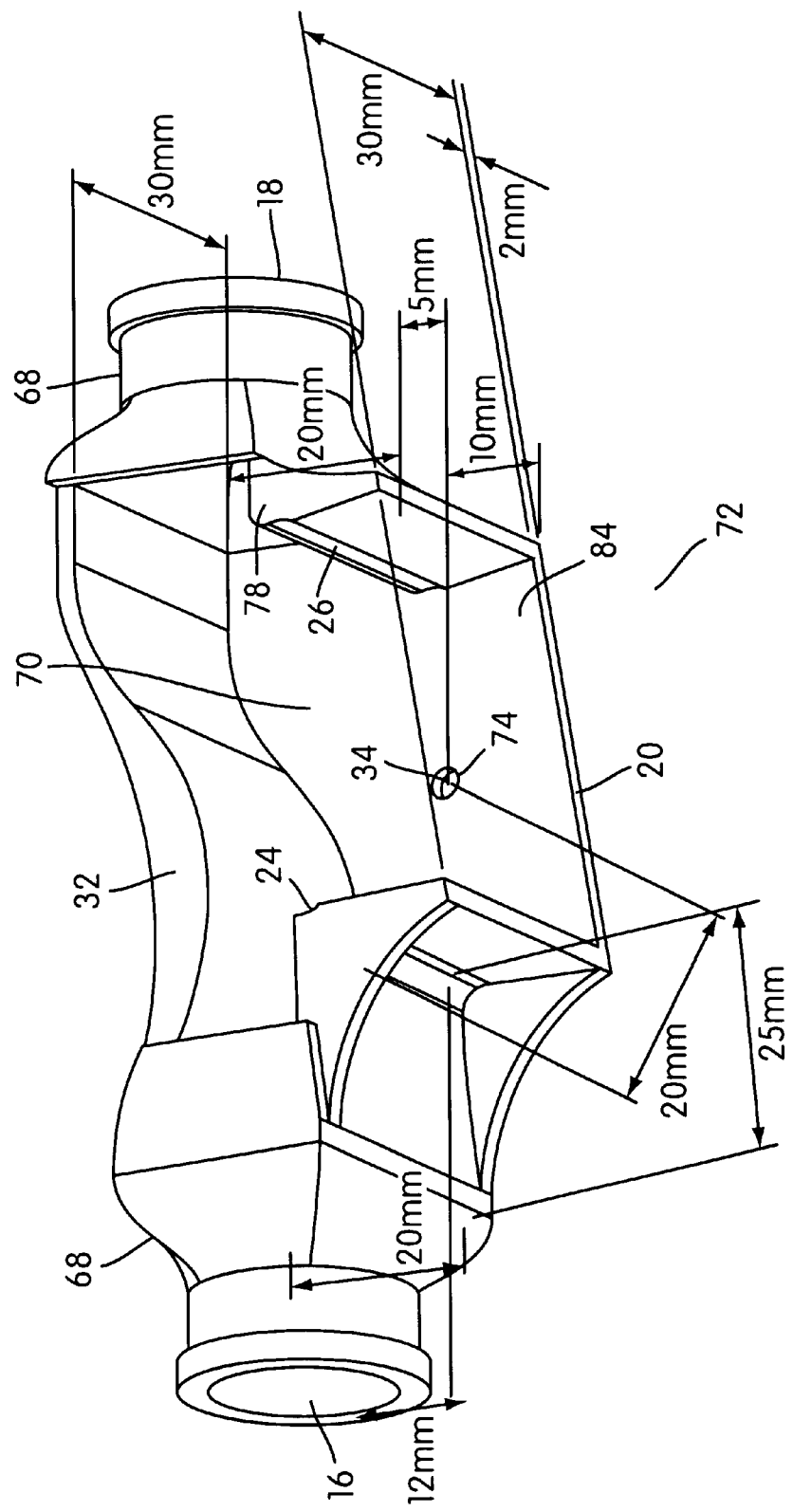
FIG. 11 is a perspective view showing additional details of the housing of FIGS. 4–5.
Figure 12:
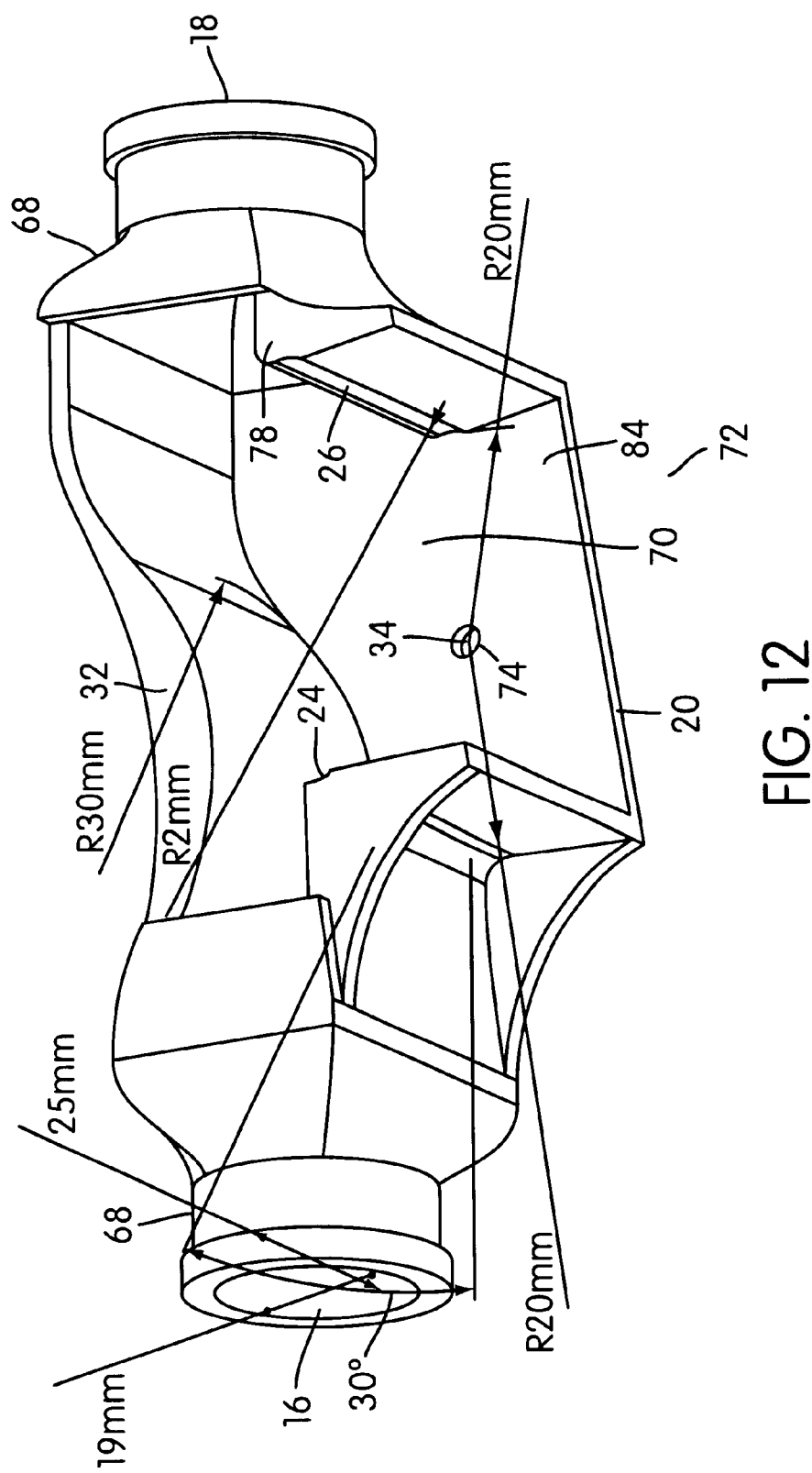
FIG. 12 is a perspective view showing additional details of the housing of FIGS. 4–5.

FIGS. 11–12 show a perspective view of the housing 14 illustrated in FIGS. 8–10, illustrating the connecting portions 68 of housing 14. The same radius and dimension measurements of FIGS. 9–10 are shown in FIGS. 11–12. Additionally, FIG. 11 shows the height of the housing 14 as 30 mm to provide a sufficient flow path in this particular embodiment. The thickness of a housing floor 84 of 2 mm was chosen to provide sufficient rigidity in this particular embodiment in the case that the housing 14 is constructed out of plastic. FIG. 12 additionally shows an internal diameter of the connecting portions 68 of 19 mm, and an external diameter of the connecting portions 68 of 25 mm, such diameters accommodating other components (not shown) connected to the connecting portions 68.

The measurements shown in FIGS. 6–7 and 9–12 are not meant to be limiting in scope, and are only shown for the illustration of one particular embodiment.

Figure 13:
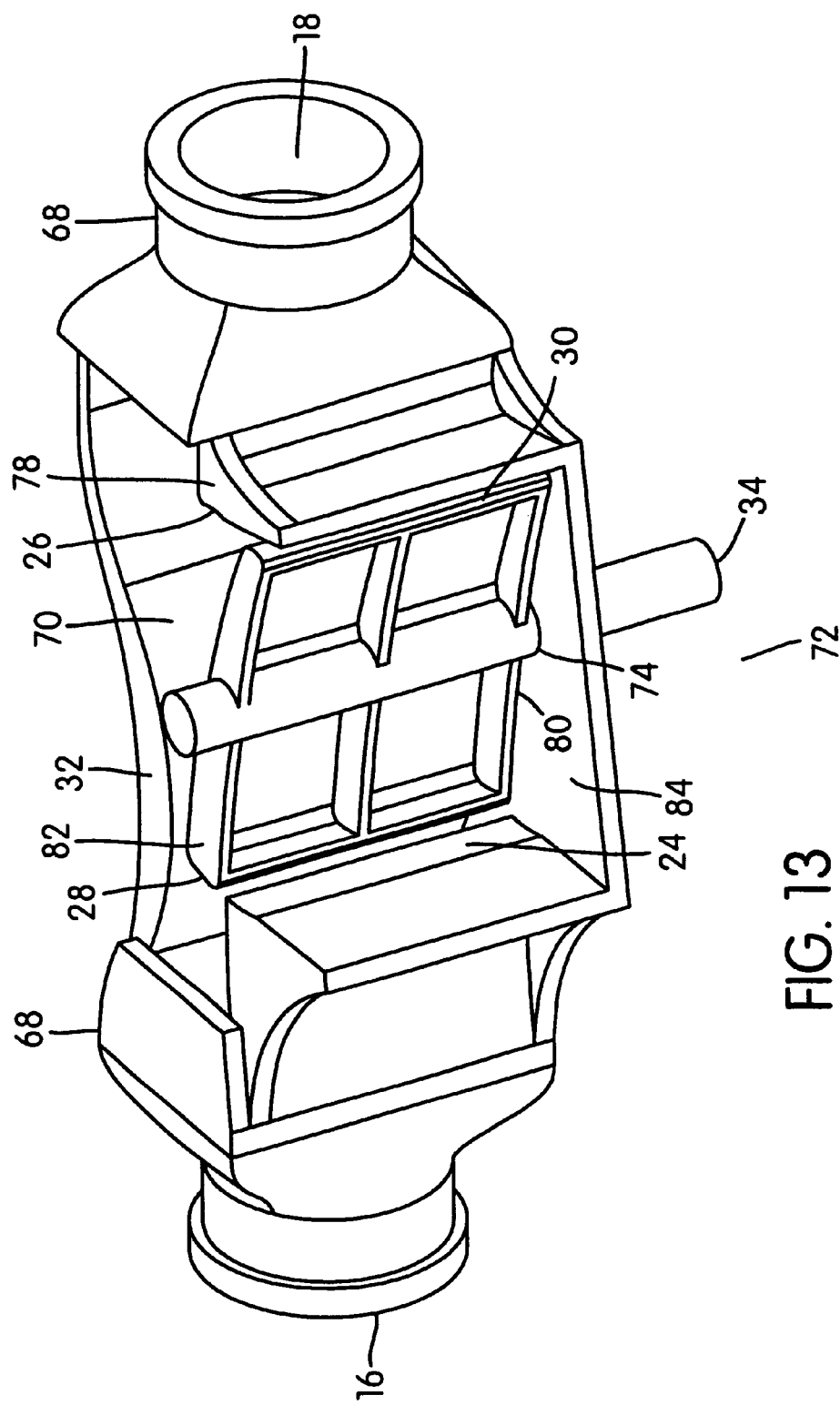
FIG. 13 is a perspective view of the flow diverter valve of FIGS. 4–5, illustrating an intermediate position.

FIG. 13 illustrates the vane 10 pivotably mounted within the housing 14 (the housing 14 shown including the connecting portions 68). The vane pivot axis 34 coincides with the housing through hole 74, allowing the vane pivot axis 34 to extend through the housing through hole 74 and protrude externally from the housing 14. A lower vane edge 80 can sealingly engage against the housing floor 84. The rotary actuator 58 mounted externally to the housing floor 84 (see FIG. 5) can rotate the vane pivot axis 34, in turn rotating the vane 10 about the vane pivot axis 34. A housing cover (not shown) with a housing cover through hole can be sealably mounted to the top surface of housing 14, enclosing the vane 10 within the housing while securing the upper portion of the vane pivot axis 34 via the housing cover through hole. The housing cover sealably engages the top surfaces of the housing 14 and an upper vane edge 82, substantially eliminating fluid communication between the housing interior 70 and the atmosphere 72.

Although the vane 10 is illustrated and described in terms of being mounted pivotably within the housing 14, the vane 10 could be bendably attached within the housing 14. In such cases, the vane 10 and/or the housing 14, or a portion of the vane 10 and/or the housing 14, can be constructed from a flexible material, allowing the vane 10 to bend about a vane attachment point. The attachment point can be positioned at any point along the vane 10, providing a central vane attachment point similar to the illustrated vane pivot axis 34, or providing a cantilever arrangement where the vane attachment point is near the leading edge 28 or trailing edge 30 of the vane 10.

In a preferred embodiment, the leading vane edge 28 and the corresponding leading housing surface 24 have substantially equal radii of curvature concentric with the vane pivot axis 34. Similarly, trailing vane edge 30 and the corresponding trailing housing surface 26 have substantially equal radii of curvature concentric with the vane pivot axis 34. Consequently, the leading vane edge 28 and the leading housing surface 24 can sealingly engage each other, depending upon the rotational position of the vane 10. The trailing vane edge 30 and the trailing housing surface 26 can also sealingly engage each other, depending upon the rotational position of the vane 10. The radii of curvature of the vane edges and housing surfaces can vary depending upon the particular embodiment.

Figure 14:
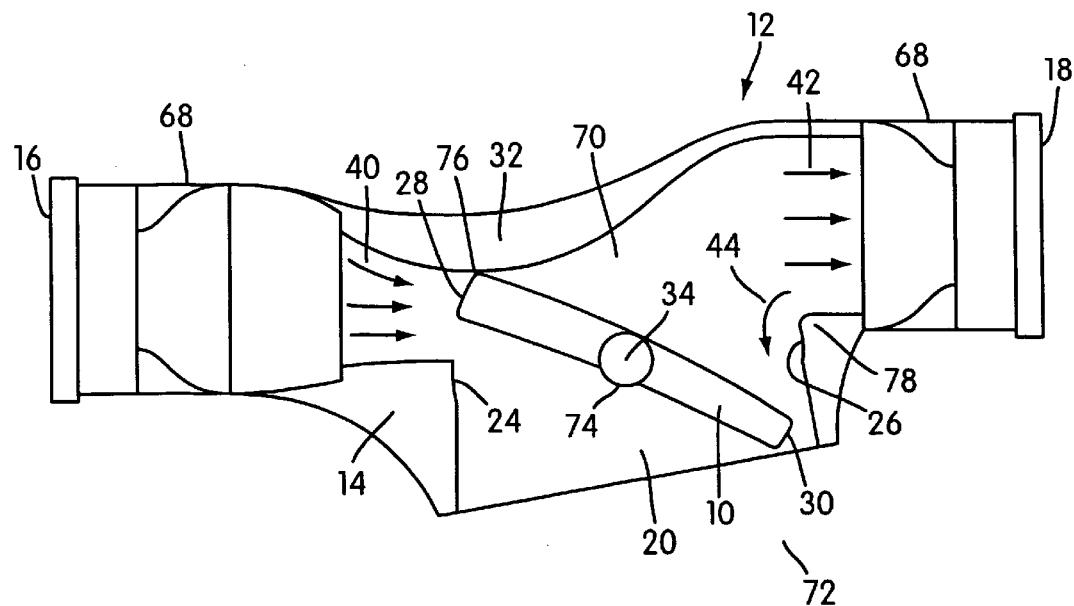
FIG. 14 is a top view of a flow diverter valve illustrating an open, venting, Expiratory Positive Airway Pressure (EPAP) position according to an embodiment of the present invention.

There are an unlimited number of intermediate positions that the vane 10 can assume between a fully open position and a fully closed position. The range of rotational movement of the vane 10 is constrained in the fully closed position by the interaction of the leading vane edge 28 with the leading housing surface 24. In the fully open position, the vane 10 is constrained by the interaction of the leading vane edge 28 with the housing bend intersection point 76 (FIGS. 9, 10 and 14). The housing bend 32 provides the advantage of reducing the range of rotational movement of the vane 10 necessary to assume the fully open position and the fully closed position. The vane may pivot about 30° in that embodiment, although it can rotate more or less depending on preference, keeping in mind that response time is decreased as the amount of rotation is decreased. Additionally, the housing bend 32 provides smooth tangential curves to the flow within the flow diverter valve 12. Housing bend 32 is confined substantially to the portion of the housing interior 70 near the inlet port 16, minimizing a reduced flow path and a resulting flow impedance to the part of the housing interior 70 near the inlet port 16. Importantly, the part of the housing interior 70 near the outlet port 18 does not have a reduced flow path and accordingly does not have unnecessary flow impedance.

In the illustrated embodiment, the engagement between the leading vane edge 28 and the leading housing surface 24 is not necessarily identical in nature to the engagement between the trailing vane edge 30 and the trailing housing surface 26. The difference between the two engagements is a result of the asymmetrical configuration of the vane 10 and housing 14 about the vane pivot axis 34. As the vane 10 rotates between the fully open position, through a plurality of intermediate positions, into the fully closed position, a leading engagement occurs between the leading vane edge 28 and the leading housing surface 24. A trailing engagement subsequently occurs between the trailing vane edge 30 and the trailing housing surface 26 as rotation of the vane 10 continues. In the illustrated embodiment, the leading and trailing engagements do not occur simultaneously as the vane 10 rotates. Additionally, the duration of the leading and trailing engagements is not equal as the vane rotates. The natures of the seals of the leading and trailing engagements are not identical during rotation of the vane 10 and/or when the vane 10 is stationary in a fully or partially sealed intermediate or fully closed position.

For example, in the illustrated embodiment shown in FIG. 13, the leading engagement occurs prior to the trailing engagement as the vane 10 rotates from the fully open position into the fully closed position, and/or any number of intermediate positions. There is a plurality of partially sealed intermediate positions of the vane 10. These positions are described by a partial seal, provided by the leading engagement between the leading vane edge 28 and the leading housing surface 24, while at the same time no seal is provided between the trailing vane edge 30 and the trailing housing surface 26. Similarly, as the vane 10 rotates in an opposite direction from the fully closed position to the fully open position, it passes through the plurality of partially sealed intermediate positions where the trailing engagement between the trailing vane edge 30 and the trailing housing surface 26 does not occur. Alternate embodiments allow the leading and trailing engagements to occur simultaneously, or allow the trailing engagement to occur while the leading engagement does not.

In the illustrated embodiment of FIGS. 4–16, the surface area of both the leading vane edge 28 and the corresponding leading housing surface 24 is greater than the surface area of both the trailing vane edge 30 and the corresponding trailing housing surface 26. Additionally, the difference between the radius of curvature of the leading vane edge 28 and the leading housing surface 24 is equal to the difference between the radius of curvature of the trailing vane edge 30 and the trailing housing surface 26. As a result, when the vane 10 is in the fully closed position or a substantially closed position, the seal of the leading engagement is greater than the seal of the trailing engagement. It is understood that the natures of the seals can be adjusted by varying the surface areas and/or the radii of curvature of the vane edges and housing surfaces. For example, the radii of curvature of the vane edges can be 20, while the radii of curvature of the housing surfaces can be 20.2. An exemplary means of adjusting the surface area of the leading vane edge 28 is by increasing or decreasing the distance between the leading vane corners 64 (FIGS. 6–7). The surface area of the trailing vane edge 30 can likewise be adjusted by varying the distance between the trailing vane corners 66.

Figure 14A:
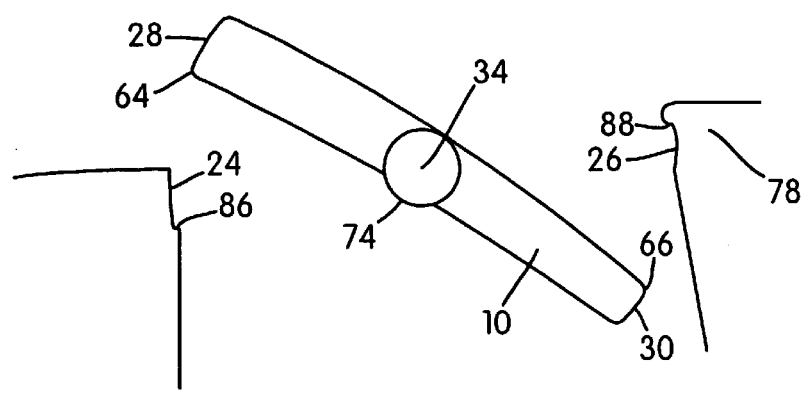
FIG. 14A is a detailed view of a portion of FIG. 14.
Figure 15:
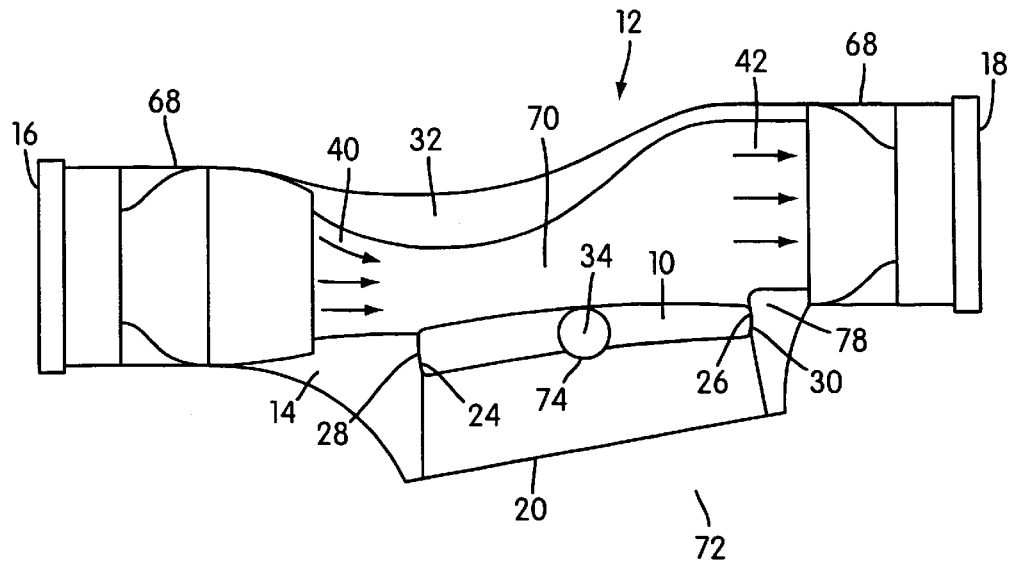
FIG. 15 is a top view of the flow diverter valve of FIG. 5 illustrating a closed, Inspiratory Positive Airway Pressure (IPAP) position.
Figure 16:
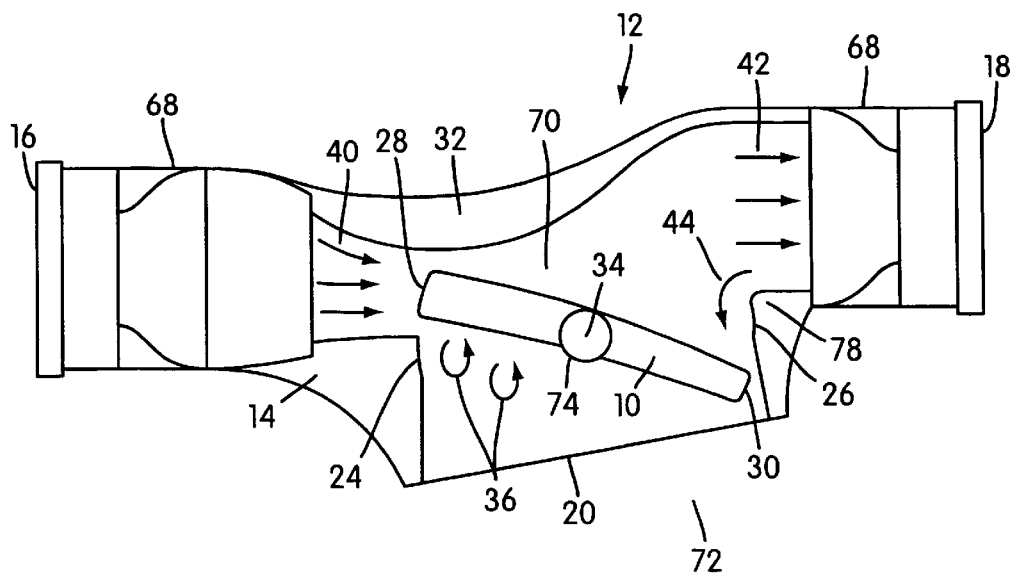
FIG. 16 is a top view of the flow diverter valve of FIG. 5, illustrating an Intermediate position.

The vane 10 can be positioned in the housing 14 in the open position (FIG. 14), the closed position (FIG. 15) and the plurality of intermediate positions, e.g., as shown in FIG. 16. In a preferred embodiment, the leading housing surface 24 and the trailing housing surface 26 are shaped to receive the leading vane edge 28 and the trailing vane edge 30, respectively, when the vane 10 is rotated about the vane pivot axis 34 into the closed position. Additionally, the radii of curvature of the leading housing surface 24 and the trailing housing surface 26 can be slightly larger than the respective radii of curvature of the leading vane edge 28 and the trailing vane edge 30. Such an arrangement provides a sufficient seal in the closed position, while allowing rotation of the vane 10 without excessive friction. The leading housing surface 24 and/or the trailing housing surface 26 can contain a leading ledge 86 and/or a trailing ledge 88 to contact the vane 10 when the vane 10 is rotated into a fully closed position. FIG. 14A shows the leading housing surface 24 and the trailing housing surface 26 in greater detail, including the leading ledge 86 and the trailing ledge 88. The vane pivot axis 34 is illustrated at a position equidistant from the leading vane edge 28 and the trailing vane edge 30. However, the vane pivot axis 34 may be located at various positions between the leading vane edge 28 and the trailing vane edge 30.

The housing 14 and vane 10 are configured such that the blower or flow generator 22 is not choked, regardless of the position of the vane 10, which means that the flow through and from the blower is not stopped or significantly slowed, e.g., when the vane 10 is in any position. This is in sharp contrast to the cammed valve member disclosed in U.S. patent application Ser. No. 09/598,053, which can choke the blower while the apparatus is in the expiration mode. Since the vane 10 does not cause choking of the blower 22, regardless of its position, the speed and response time when shifting from the expiration phase to the inspiration phase can be made faster, thereby improving patient comfort and decreasing power consumption. Stated differently, the blower 22 remains substantially unchoked as the vane 10 moves between the open and closed positions. In another sense, it can be said that the blower is not choked, at least in part, because the flow capacity of the housing 14 downstream of the vane 10 is at least substantially equal to flow capacity upstream of the vane 10, regardless of the position of the vane 10. Because the flow created by the blower 22 passes to the outlet port and/or the exhaust port during all positions of the vane 10, the blower 22 remains substantially unchoked. Moreover, flow continues through the blower itself regardless of the position of the vane 10.

Turbulence can be associated with eddying motion of fluid. The vane 10 is shaped to minimize flow turbulence generated by interactions between the leading vane edge 28 and the trailing vane edge 30 with the flow 40 from the inlet port 16. Accordingly, the shape of the vane 10 reduces noise, pressure fluctuations, and flow fluctuations associated with flow turbulence. Additionally, the radiused leading vane corners 64 and trailing vane corners 66 (FIGS. 6–7) reduce the generation of flow separation associated with turbulence. The vane 10 and the housing 14 are configured to minimize pressure fluctuations and flow fluctuations, especially in flow 42 to the outlet port 18. In the closed position, leading vane edge 28 and trailing vane edge 30 are flush with leading housing surface 24 and trailing housing surface 26, respectively. Turbulence is minimized by the smooth tangential curves of the housing 14, and also by ensuring that the vane 10 has an angle to flow 40 from the inlet port 16 not exceeding approximately 15°–25° (except when completely shutting off flow 42 to the outlet port 18 in the fully open position). Preferably, the vane 10 has an angle to flow 40 from the inlet port 16 not exceeding 20°.

In operation, flow generator 22 provides a flow of air or breathable gas to the flow diverter valve 12 via the inlet port 16. The vane 10 variably diverts the flow 40 from the inlet port 16 to the exhaust port 20 and/or the outlet port 18. The flow 42 diverted to the outlet port 18 is conducted to the patient mask 54 via the conduit 52. The vane 10 is caused to move rotatably about the vane pivot axis 34 within a defined range by the rotary actuator 58 (FIG. 4). A servo motor, preferably incorporating a sensor indicative of the angular position of the vane pivot axis 34, can be used as the rotary actuator 58. Pressure feedback loops used for servo control of the position of the vane 10 automatically compensate for any pressure changes due to variation in fluid viscosity caused by temperature, humidity, or gas composition changes. The pressures used in the pressure feedback loops can be taken from the flow meter 50, or from the inlet port 16 and the outlet port 18, depending upon the particular embodiment of the ventilatory assistance apparatus 11.

The housing bend 32 provides the benefit of a smaller rotational range of the vane 10, resulting in reduced time necessary for the vane 10 to rotate about the vane pivot axis 34 between the open position and the closed position. In one embodiment, the range of vane rotation is generally within approximately 25°–35°, preferably 30°, providing a reduced response time compared to a larger range of vane rotation. However, the housing bend 32 and the housing bend intersection point 76 can be designed to vary the rotational range of the vane 10. For example, the radius of curvature of the housing bend 32 can be varied, in addition to varying the distance between the housing bend intersection point 76 and the leading housing surface 24. The angular distance between the housing surface 24 and the housing bend 32, as measured from the vane pivot axis 34, can thereby be reduced. Additionally, the dimensions of the vane 10, such as the radii of curvature of the vane edges and the distance between the leading vane corners 64, can be varied to affect the rotational range of the vane 10 constrained by the housing bend 32.

It is preferable to provide a low impedance flow path between the inlet port 16 and the outlet port 18. Therefore, the housing bend 32 is configured to allow passage of the flow 40 from the inlet port 16 to the outlet port 18 without excessive impedance to flow. The housing bend 32 is also configured to present smooth tangential curves along the flow path between the inlet port 16 and the outlet port 18, thereby providing a low impedance path from the inlet port 16 to the outlet port 18, while providing the benefit of reduced rotation of the vane 10 about the vane pivot axis 34.

The shape of the housing 14, in cooperation with the housing bend 32, can also be configured to direct undiverted flow 40 from the inlet port 16 to the outlet port 18, the exhaust port 20, or a combination of the outlet port 18 and the exhaust port 20. In the embodiment of FIGS. 4–16, the housing bend 32 partially directs the flow 40 from the inlet port 16 towards the exhaust port 20 when the vane 10 is at least partially open.

As the vane 10 is rotated to variably divert the flow 40 from the inlet port 16 to the outlet port 18, the flow diverter valve 12 operates typically in an inspiratory and/or an expiratory capacity. The rotational position of the vane 10 associated with a particular pressure and/or flow rate at the outlet port 18 is dependent upon pressure and/or flow rate at the inlet port 16. An outlet pressure and/or flow rate associated with either inspiratory or expiratory operation of the flow diverter valve 12 depends upon individual pressures determined for a patient either by a doctor or by using an autosetting machine in accordance with patient need. However, in the fully open position, substantially none of the flow 40 from the inlet port 16 is diverted to the outlet port 18 and ultimately to the patient mask 54. This zero flow condition corresponds to an EPAP level of 0 cm $H_2O$. In practice, an EPAP level of 0 cm $H_2O$ is not used for normal treatment. Rather, the EPAP level is approximately 2–12 cm $H_2O$, and preferably 1–5 cm of $H_2O$. However, this is generally a clinical issue and not limited by the design of the flow diverter valve 12.

Generally, for the expiratory phase of the patient respiratory cycle, the vane 10 is rotated into a plurality of intermediate positions near the fully open position, to provide a substantially smaller amount of flow 42 to the outlet port 18. Additionally, the vane 10 provides a low impedance path for exhaled back flow 44 to the atmosphere 72. This condition corresponds to an EPAP level of approximately 2–12 cm $H_2O$, and preferably 1–5 cm $H_2O$. For the inspiratory phase of the patient respiratory cycle, the vane 10 is rotated into the closed position or a plurality of intermediate positions near the fully closed position. This condition results in the vane 10 diverting a substantially larger amount of the flow from the flow generator 22 to the patient, corresponding to an IPAP level of approximately 15–30 cm $H_2O$.

FIG. 14 illustrates the flow diverter valve 12 with the vane 10 rotated about the vane pivot axis 34 into the open position, e.g., a venting position. The vane 10 is pivotably rotated about the vane pivot axis 34 to divert the flow 40 from the inlet port 16 to the exhaust port 20. In particular, while venting the flow 40 from the inlet port 16 to the atmosphere, the vane 10 protrudes into a flow path between the inlet port 16 and the outlet port 18, the protrusion limited by abutment with the housing bend 32. The position of the vane pivot axis 34 along the vane 10 allows a low impedance path for flow on both sides of the vane 10 when the vane 10 is in a non-closed position, i.e., the flow diverter valve 12 can exhaust flow 40 from the inlet port 16 to the atmosphere 72, while simultaneously exhausting exhaled back flow 44 from the patient mask via the outlet port 18 to the atmosphere 72.

During operation in the open position, a low positive pressure occurs at the outlet port 18. The illustrated embodiment is shown in FIG. 14 with the leading vane edge 28 contacting the housing bend 32. Even with such contact between the vane 10 and the housing bend 32, a substantially low portion of flow 40 from the inlet port 16 can flow to the outlet port 18. A seal or gasket (not shown) fitted to either the housing 14 or the vane 10 can alternatively be used to ensure zero flow to the outlet port 18. However, zero flow to the outlet port 18 is not generally used during patient treatment. In practice, substantially open positions of the vane 10 nearly contacting housing bend 32 represent a positive pressure at the outlet port 18 of approximately 2–12 cm $H_2O$, and preferably 1–5 cm $H_2O$. Such a pressure is typically associated with the expiratory phase of the respiration cycle. In this open position, a majority of the flow 40 from the inlet port 16 is diverted to the exhaust port 20 and out to the atmosphere 72. Additionally, the vane 10 provides a low impedance exhalation path via the exhaust port 20 for the back flow 44 from the outlet port 18, so the back flow 44 exhaled by the patient at the patient mask 54 can be vented to atmosphere without patient discomfort.

FIG. 15 illustrates the flow diverter valve 12 with the vane 10 rotated about the vane pivot axis 34 into a fully closed position, whereby the air or breathable gas diverted from the inlet port 16 to the outlet port 18 is maximized. This closed position represents the maximum pressure at the outlet port 18, typically 20–30 cm $H_2O$, and preferably 15–30 cm $H_2O$, for CPAP treatment, and is generally used during an inspiratory phase of the respiration cycle. The leading housing surface 24 and the trailing housing surface 26 can be fitted with a seal or gasket (not shown) to sealingly engage the leading vane edge 28 and the trailing vane edge 30 when the vane 10 is moved into the fully closed position. Alternatively and/or additionally, the vane 10 can be fitted with a seal or gasket (not shown) to sealingly engage the housing surfaces. Such a seal or gasket could provide complete diversion of the flow 40 from the inlet port 16 in the fully closed position, but is generally not necessary during patient treatment.

The leading housing surface 24 can be shaped to provide the leading ledge 86 (FIG. 14A) that protrudes into the exhaust port towards the vane pivot axis 34, so as to contact the lower leading vane corner 64 when the vane 10 is rotated into the fully closed position. The trailing housing surface 26 can similarly be shaped with the trailing ledge 88 to contact the upper trailing vane corner 66 when the vane 10 is rotated into the fully closed position. Such ledges can provide an abutment for the vane 10, as well as improved sealing between the vane edges and the housing surfaces without unnecessary impediment to the rotation of the vane 10.

In the closed position of the illustrated embodiment, the vane 10 forms a portion of a passageway leading from the inlet port 16 to the outlet port 18 and diverts nearly all of the flow 40 from the inlet port 16 to the outlet port 18. The leading vane edge 28 and trailing vane edge 30 can engage the leading housing surface 24 and trailing housing surface 26, respectively, in the closed position. This closed position engagement between the leading vane edge 28 and trailing vane edge 30, and the leading housing surface 24 and trailing housing surface 26, minimizes leakage of the flow 40 from the inlet port 16 past the vane 10 into the exhaust port 20. Alternatively, the radii of curvature of the leading vane edge 28 and the trailing vane edges 30, and/or the radii of curvature of the leading housing surface 24 and the trailing housing surface 26, can be chosen such that the leading vane edge 28 and the trailing vane edge 30 nearly contact the leading housing surface 24 and the trailing housing surface 26, respectively, without touching them. It is desirable to allow rotation of the vane 10 without unnecessary impediment, allowing a reduced response time necessary for the vane 10 to change position and decreased power requirements for the rotary actuator 58.

By controlling the rotation of the vane 10 via pressure feedback loops (known in the art), different output treatment pressures can be obtained for a given constant pressure at the inlet port 16, as required by the patient. A range of output pressures at the outlet port 18, to be transmitted via the conduit 52 to the patient mask 54, can be appropriately selected for implementation of CPAP. Higher inspiratory pressures generally correspond with the vane 10 being rotated into a substantially closed position, as illustrated in FIG. 15, whereby the flow diverter valve 12 diverts a majority of the flow 40 from the inlet port 16 to the outlet port 18. Additionally, the vane 10 can be rotated into a partially closed and/or partially opened intermediate position during IPAP, if a lower inspiratory pressure is desired. The position of the vane 10 chosen depends upon the pressure feedback loops used for servo control of the rotary actuator 58. The open position, or an intermediate position, of the vane 10 allows venting of the flow 40 from the inlet port 16 to the atmosphere 72 via the exhaust port 20. Accordingly, the pressures at the outlet port 18 obtained with the vane 10 in the plurality of intermediate positions are lower than the pressures obtained when the vane 10 is in a substantially closed position.

An expiratory positive airway pressure of 0 cm $H_2O$ is generally not used for normal patient treatment. Therefore, it is not always necessary to obtain an outlet port pressure and/or flow of zero by diverting all of the flow 40 from the inlet port 16 to the exhaust port 20. Accordingly, there is no absolute need for the leading vane edge 28 to contact the housing bend 32 in the open position, and a smaller, lighter vane with a reduced response time can be used. However, it is understood that the vane 10 could be configured so that the vane surface 28 contacts the housing bend 32 in the open position, if necessary.

Turbulence can be caused by flow separation, which can arise when surfaces of the housing 14 or the vane 10 are presented to the flow 40 from the inlet port 16 at angles greater than approximately 15°–25°. FIG. 16 illustrates the flow diverter valve 12 with the vane 10 placed in an intermediate position both partially diverting the flow 40 from the inlet port 16 to the outlet port 18 and partially venting the flow 40 from the inlet port 16 to the exhaust port 20. Exhaled back flow 44 from the outlet port 18 is vented to the atmosphere 72 via exhaust port 20 in the illustrated intermediate position of the vane 10. Turbulence caused by flow separation 36 occurs within the exhaust port 20. However, the vane 10 confines flow separation 36 to the exhaust port 20 of the flow diverter valve 12. Disadvantages including noise and flow fluctuation associated with flow separation 36 are accordingly confined to the exhaust port 20, isolated away from the flow 42 to the outlet port 18. Importantly, turbulence and fluctuations of flow within the flow meter 50 are minimized. This provides the benefit of improved flow determination accuracy and/or speed, and increased patient comfort and compliance with treatment.

The housing bend 32 provides an additional benefit that turbulence in the flow 42 to the outlet port 18 is minimized when the vane 10 is in the open or intermediate positions. The flow 40 from the inlet port 16 that flows between the leading vane edge 28 and the housing bend 32 in the open or intermediate positions is presented with surfaces at no greater than approximately 15°–25° to the flow 40 from the inlet port 16, substantially eliminating flow separation. As illustrated in FIG. 16, the housing bend 32 redirects a portion of the flow 40 from the inlet port 16 in a direction approximately coplanar with the vane 10, reducing the angle of incidence between the flow 40 from the inlet port 16 and the vane 10. The reduced angle of incidence minimizes separation of the flow 40 and resultant turbulence on a side of the vane 10 exposed to the outlet port 18, minimizing noise and pressure fluctuations associated with flow separation in the flow 42 to the outlet port 18.

Minimizing flow fluctuations is significant because flow fluctuations introduce disadvantages such as noise into the calculations used to determine flow. Accounting for any flow fluctuation noise in the flow 42 to the outlet port 18 during flow calculation requires extra signal processing as well as extra time. Therefore, minimizing flow fluctuations provides advantages including reduced flow calculation circuitry and reduced response time, particularly important in the pressure feedback loops used to control the position of the vane 10.

The materials of the housing 14 can be constructed from castable metals such as stainless steel, aluminum or magnesium as well as injection moldable polymers such as polycarbonate, polypropylene, glass reinforced nylon or epoxy, or any other suitable medical grade plastic. The vane 10 has similar requirements, with the understanding that it may be preferable to construct the vane 10 with materials that are lightweight. Such preference depends upon the desired response speed and the characteristics of the rotary actuator 58 used to rotate the vane 10. The surface texture of the housing interior 70 and the vane 10 is preferably smooth to reduce flow impedance. Additionally, the textures of the housing interior 70, the lower vane edge 80 and the upper vane edge 82 that come in contact with the housing interior 70 are preferably smooth to provide sufficient seals while reducing friction, wear, impeded movement of the vane 10, and contact pressure necessary to provide the sufficient seals.

While preferred embodiments of the invention have been described with reference to specific examples, it will be appreciated by those skilled in the art that the invention may be embodied in many other forms.

Figure 17:
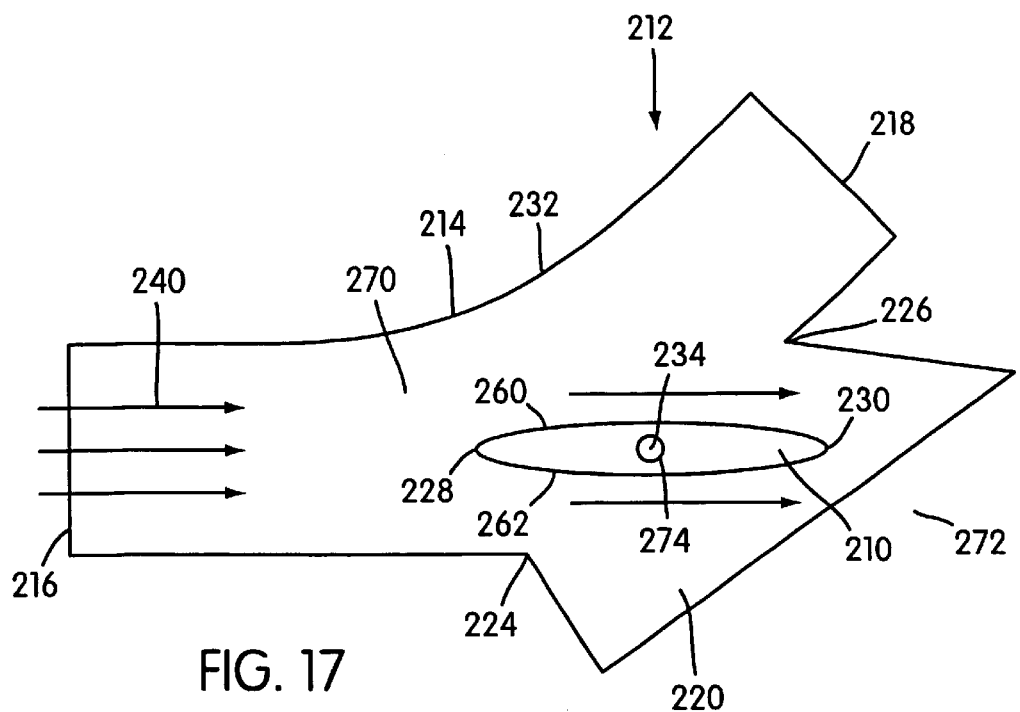
FIG. 17 is a top view of a flow diverter valve illustrating an open, venting, Expiratory Positive Airway Pressure (EPAP) position according to another embodiment of the present invention.
Figure 18:
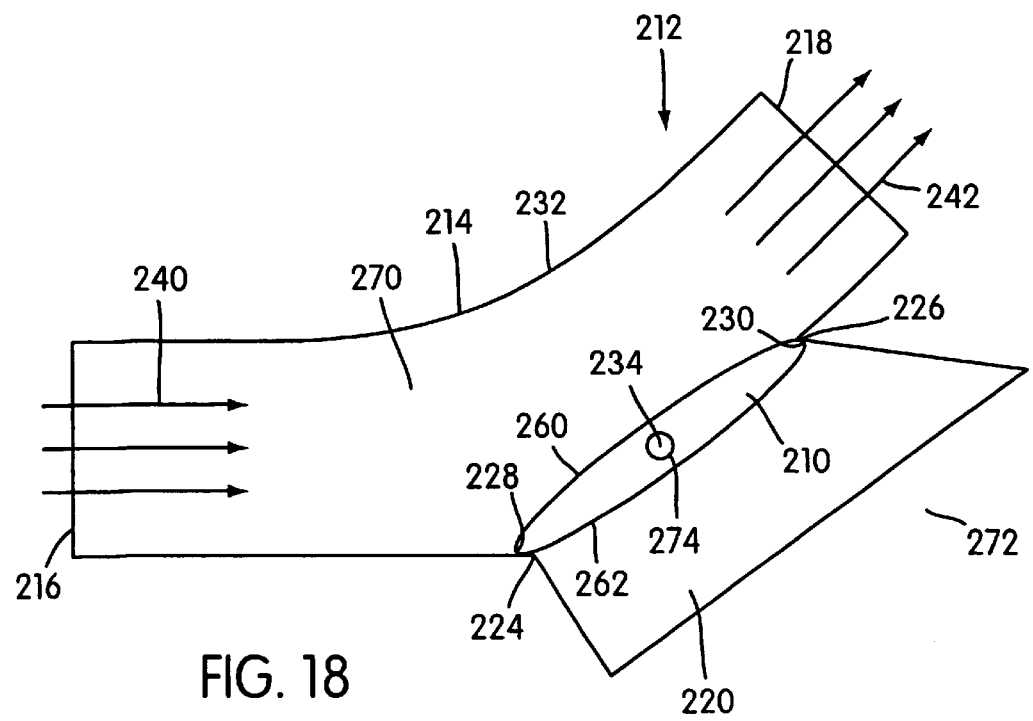
FIG. 18 is a top view of the flow diverter valve of FIG. 17, illustrating a closed, Inspiratory Positive Airway Pressure (IPAP) position.
Figure 19:
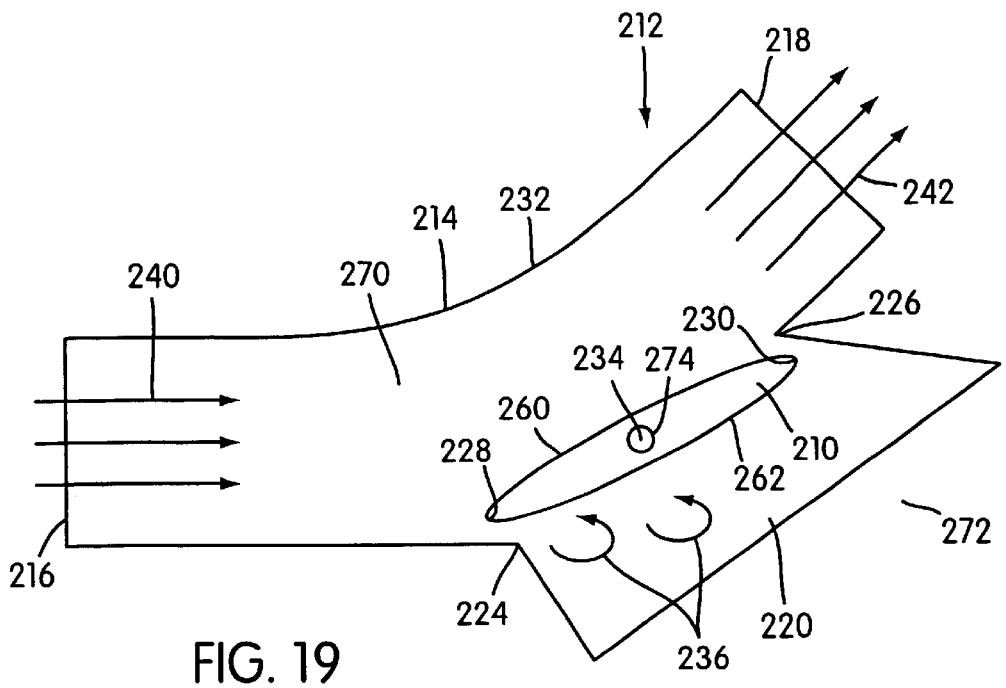
FIG. 19 is a top view of the flow diverter valve of FIG. 17, illustrating an intermediate position.

For example, FIGS. 17–19 illustrate the flow diverter valve 12 of FIGS. 4–16 in an alternative embodiment. In particular, an exhaust port 220 of a flow diverter valve 212 is disposed in line with flow 240 from an inlet port 216, and an outlet port 218 is disposed at an angle greater than zero to the flow 240 from the inlet port 216. Additionally, a housing 214 with a housing bend 232, and a vane 210 are disposed so that when in an open position, illustrated in FIG. 17, the vane 210 does not divert the flow 240 from the inlet port 216 in a direction other than the original direction of the flow 240 from the inlet port 216. The vane 210 is shown with a first side vane surface 260 and a second side vane surface 262 with radii of curvature that are approximately equal. While not illustrated, it is understood that the radius of curvature of the first side vane surface 260 could be larger than the radius of curvature of the second side vane surface 262. Additionally, it is understood that the vane 210 could be configured to contact the housing 214 or the housing bend 232 in the open position, if necessary to provide complete diversion of the flow 240 from the inlet port 216 to the atmosphere 272. In a closed position, illustrated in FIG. 18, the vane 210 diverts a majority of the flow 240 from the inlet port 216 to the outlet port 218.

FIG. 19 illustrates the flow diverter valve 212 with the vane 210 placed in a position both partially diverting the flow 240 from the inlet port 216 to the outlet vent 218 and partially venting the flow 240 from the inlet port 216 to the exhaust port 220. As illustrated, flow separation 236 occurs, caused by a leading portion of the vane 210 protruding into undiverted flow 240 from the inlet port 216 at an angle greater than approximately 15–25° to the flow 240 from the inlet port 216. The flow separation 236 does not occur on a side of the vane 210 facing the outlet port 218.

The flow separation 236 occurs on a side of the vane 210 facing the exhaust port 220. Accordingly, turbulence caused by the flow separation 236 is confined to the exhaust port 220, isolated from flow 242 diverted to the outlet port 218. Fluctuations in the flow 242 to the outlet port 218 are thereby minimized. Additionally, the exhaust port 220 can be fitted with a filter or muffler component (not shown), further minimizing noise produced by the flow diverter valve 212.

Figure 20:
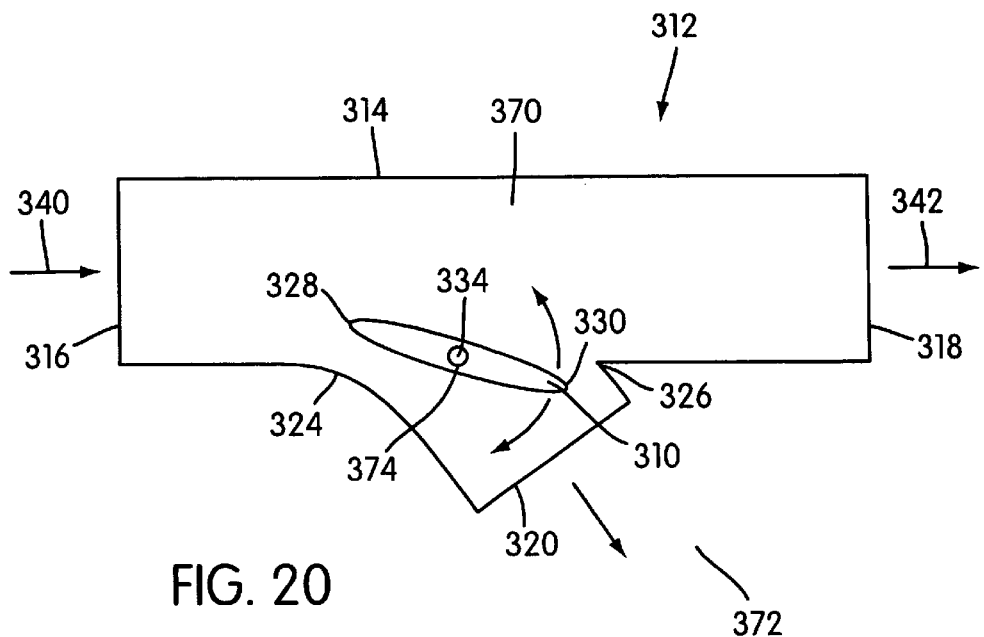
FIG. 20 is a top view of a flow diverter valve according to yet another embodiment of the present invention.

FIG. 20 illustrates the flow diverter valve 12 of FIGS. 4–16 in yet another embodiment. In this embodiment, an outlet port 318 of a flow diverter valve 312 is disposed in line with flow 340 from an inlet port 316, and an exhaust port 320 is disposed at an angle greater than zero to the flow 340 from the inlet port 316. Additionally, a housing 314 and a vane 310 are disposed so that when in the closed position, the vane 310 and the housing 314 do not substantially alter the direction of the flow 340 from the inlet port 316. In the open position, the vane 310 protrudes into the flow 340 from the inlet port 316, diverting at least a portion of the flow 340 from the inlet port 316 into the exhaust port 320 where it is vented to the atmosphere 372.

It can thus be appreciated that the objectives of the present invention have been fully and effectively accomplished. The foregoing specific embodiments have been provided to illustrate principles of the present invention and are not intended to be limiting. To the contrary, the present invention is intended to encompass all modification, alterations, and substitutions within the spirit and scope consistent with the principles and novel features disclosed in any fashion herein.

What is claimed is:

1. A valve assembly for use in a ventilator, the valve assembly comprising a housing and a rotatable vane for directing the flow of air within the housing,
   the housing having an inlet port for receiving a flow of pressurized air from a blower, an outlet port for delivering air to a patient interface and an exhaust port,
   the vane being rotatable between a first angular position and a second angular position without choking the blower, wherein:
   (i) in the first angular position substantially all of the flow of air received at the inlet port is directed by the vane to the exhaust port,
   (ii) in the second angular position substantially all of the flow of air received at the inlet port is directed by the vane to the outlet port,
   (iii) in angular positions intermediate of the first and second angular positions, a fraction of the flow of air received at the inlet port is directed by the vane to the exhaust port and a complementary fraction of the flow of air received at the inlet port is directed by the vane to the outlet port, and
   (iv) an arc through which the vane moves between the first and second angular positions is approximately 30 degrees.

2. The valve assembly of claim 1, wherein the vane forms a portion of a passageway between the inlet port and the outlet port when in the second angular position.

3. The valve assembly of claim 1, wherein the vane can selectively direct undiverted flow from the inlet port to at least one of the exhaust port and the outlet port when the vane is between the first angular position and the second angular position.

4. A ventilatory assistance apparatus, comprising:
a flow generator; and
a flow diverter valve in communication with the flow generator, the flow diverter valve including a housing defining an inlet port, an outlet port and an exhaust port positioned between the inlet port and the outlet port and configured to exhaust at least one of flow from the inlet port and back flow from the outlet port, and a vane moveable between an open position and a closed position, wherein:
the vane can selectively protrude into the flow from the inlet port and thereby variably divert the flow from the inlet port to at least one of the exhaust port and the outlet port, and the vane forms a portion of a passage leading to the outlet port when in the closed position, and
the housing includes a housing bend that extends towards the vane into the flow from the inlet port.

5. The apparatus of claim 4, wherein the housing bend defines a stop for the vane in the open position.

6. The apparatus of claim 4, further comprising an apparatus body including a side wall with an opening aligned with the exhaust port.

7. The apparatus of claim 4, wherein the flow generator includes a blower that remains substantially unchoked as the vane moves between the open position and the closed position.

8. A ventilatory assistance apparatus, comprising:
a flow generator; and
a flow diverter valve in communication with the flow generator, the flow diverter valve including a housing defining an inlet port, an outlet port and an exhaust port positioned between the inlet port and the outlet port and configured to exhaust at least one of flow from the inlet port and back flow from the outlet port, and a vane moveable between an open position and a closed position, wherein:
the vane can selectively protrude into the flow from the inlet port and thereby variably divert the flow from the inlet port to at least one of the exhaust port and the outlet port, and the vane forms a portion of a passage leading to the outlet port when in the closed position, and
the housing includes at least one of a leading housing ledge and a trailing housing ledge that defines a stop for the vane in the closed position.

9. A ventilatory assistance apparatus, comprising:
a flow generator; and
a flow diverter valve in communication with the flow generator, the flow diverter valve including a housing defining an inlet port, an outlet port and an exhaust port positioned between the inlet port and the outlet port and configured to exhaust at least one of flow from the inlet port and back flow from the outlet port, and a vane moveable between an open position and a closed position, wherein:
the vane can selectively protrude into the flow from the inlet port and thereby variably divert the flow from the inlet port to at least one of the exhaust port and the outlet port, and the vane forms a portion of a passage leading to the outlet port when in the closed position, and
the housing has smooth tangentially curved inside surfaces with a low angle of incidence to the flow from the inlet port.

10. A ventilatory assistance apparatus, comprising:
a flow generator;
a flow diverter valve in communication with the flow generator, the flow diverter valve including a housing defining an inlet port, an outlet port and an exhaust port positioned between the inlet port and the outlet port and configured to exhaust at least one of flow from the inlet port and back flow from the outlet port, and a vane moveable between an open position and a closed position, and
a flow meter downstream of the flow diverter valve, wherein:
the vane can selectively protrude into the flow from the inlet port and thereby variably divert the flow from the inlet port to at least one of the exhaust port and the outlet port, and the vane forms a portion of a passage leading to the outlet port when in the closed position.

11. A flow diverter valve, comprising:
a housing defining an inlet port and an outlet port;
an exhaust port positioned between the inlet and outlet ports; and
a vane moveable between an open position and a closed position, wherein:
the vane can selectively protrude into the flow from the inlet port and thereby variably divert the flow from the inlet port to at least one of the exhaust port and the outlet port,
the vane forms a portion of a passage leading to the outlet port when in the closed position, and
the housing includes at least one of a leading housing ledge and a trailing housing ledge that defines a stop for the vane in the closed position.

12. The flow diverter valve of claim 11, wherein the housing includes a straight inlet port flow path from the inlet port to the exhaust port directing a majority of undiverted flow from the inlet port to the exhaust port.

13. A flow diverter valve, comprising:
a housing defining an inlet port and an outlet port;
an exhaust port positioned between the inlet and outlet ports; and
a vane moveable between an open position and a closed position, wherein:
the vane can selectively protrude into the flow from the inlet port and thereby variably divert the flow from the inlet port to at least one of the exhaust port and the outlet port,
the vane forms a portion of a passage leading to the outlet port when in the closed position, and
the vane is pivotable between the open position and the closed position.

14. A flow diverter valve, comprising:
a housing defining an inlet port and an outlet port;
an exhaust port positioned between the inlet and outlet ports; and
a vane moveable between an open position and a closed position, wherein:
the vane can selectively protrude into the flow from the inlet port and thereby variably divert the flow from the inlet port to at least one of the exhaust port and the outlet port,
the vane forms a portion of a passage leading to the outlet port when in the closed position, and
the vane comprises a flexible material that can bend, the vane being bendable between the open position and the closed position.

15. A flow diverter valve, comprising:

a housing defining an inlet port and an outlet port;

an exhaust port positioned between the inlet and outlet ports; and a vane moveable between an open position and a closed position, wherein:

the vane can selectively protrude into the flow from the inlet port and thereby variably divert the flow from the inlet port to at least one of the exhaust port and the outlet port, the vane forms a portion of a passage leading to the outlet port when in the closed position, and the housing includes a straight inlet port flow path from the inlet port to the outlet port directing a majority of undiverted flow from the inlet port to the outlet port.

16. A flow diverter valve, comprising:

a housing defining an inlet port and an outlet port;

an exhaust port positioned between the inlet and outlet ports; and a vane moveable between an open position and a closed position, wherein:

the vane can selectively protrude into the flow from the inlet port and thereby variably divert the flow from the inlet port to at least one of the exhaust port and the outlet port, and the vane forms a portion of a passage leading to the outlet port when in the closed position, and the vane has a first side surface and a second side surface with a first radius of curvature and a second radius of curvature.

17. The flow diverter valve of claim 16, wherein the first radius of curvature is equal to the second radius of curvature.

18. The flow diverter valve of claim 16, wherein the first radius of curvature is greater than the second radius of curvature.

19. The flow diverter valve of claim 16, wherein the first radius of curvature is less than the second radius of curvature.

20. The flow diverter valve of claim 19, wherein the first radius of curvature is approximately 120 mm and the second radius of curvature is approximately 200 mm.

* * * * *